United States Patent
Reddy et al.

(10) Patent No.: US 9,101,638 B2
(45) Date of Patent: Aug. 11, 2015

(54) BORONIC ACID DERIVATIVES AND THERAPEUTIC USES THEREOF

(71) Applicant: Rempex Pharmaceuticals, Inc., San Diego, CA (US)

(72) Inventors: Raja Reddy, San Diego, CA (US); Tomasz Glinka, Cupertino, CA (US); Maxim Totrov, San Diego, CA (US); Scott Hecker, Del Mar, CA (US)

(73) Assignee: Rempex Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/829,687

(22) Filed: Mar. 14, 2013

(65) Prior Publication Data

US 2014/0194382 A1    Jul. 10, 2014

Related U.S. Application Data

(60) Provisional application No. 61/749,210, filed on Jan. 4, 2013.

(51) Int. Cl.
| | |
|---|---|
| A61K 31/69 | (2006.01) |
| A61K 45/06 | (2006.01) |
| C07F 5/02 | (2006.01) |
| A61K 31/407 | (2006.01) |
| A61K 31/4196 | (2006.01) |
| A61K 31/427 | (2006.01) |
| A61K 31/546 | (2006.01) |

(52) U.S. Cl.
CPC ............... *A61K 31/69* (2013.01); *A61K 31/407* (2013.01); *A61K 31/4196* (2013.01); *A61K 31/427* (2013.01); *A61K 31/546* (2013.01); *A61K 45/06* (2013.01); *C07F 5/02* (2013.01)

(58) Field of Classification Search
CPC ........... A61K 31/69; A61K 45/06; C07F 5/02
USPC ............... 514/64; 544/229; 546/13; 548/110; 562/432
See application file for complete search history.

(56) References Cited

U.S. PATENT DOCUMENTS

| | | | |
|---|---|---|---|
| 4,194,047 | A | 3/1980 | Christensen et al. |
| 4,260,543 | A | 4/1981 | Miller |
| 4,409,214 | A | 10/1983 | Takaya et al. |
| 4,822,786 | A | 4/1989 | Zama et al. |
| 5,888,998 | A | 3/1999 | Maiti et al. |
| 6,184,363 | B1 | 2/2001 | Shoichet et al. |
| 6,586,615 | B1 | 7/2003 | Kettner et al. |
| 7,271,186 | B1 | 9/2007 | Shoichet et al. |
| 7,439,253 | B2 | 10/2008 | Lampilas et al. |
| 7,582,621 | B2 | 9/2009 | Baker et al. |
| 7,612,087 | B2 | 11/2009 | Aszodi et al. |
| 8,680,136 | B2 | 3/2014 | Hirst et al. |
| 2004/0019203 | A1 | 1/2004 | Micetich et al. |
| 2004/0157826 | A1 | 8/2004 | Lampilas et al. |
| 2005/0020572 | A1 | 1/2005 | Aszodi et al. |
| 2006/0019116 | A1 | 1/2006 | Conley et al. |
| 2006/0178357 | A1 | 8/2006 | Buynak et al. |
| 2006/0210883 | A1 | 9/2006 | Chen et al. |
| 2010/0056478 | A1 | 3/2010 | Desarbre et al. |
| 2010/0120715 | A1 | 5/2010 | Burns et al. |
| 2010/0256092 | A1 | 10/2010 | Xia et al. |
| 2011/0288063 | A1 | 11/2011 | Maiti et al. |
| 2012/0040932 | A1 | 2/2012 | Hirst et al. |
| 2013/0316978 | A1 | 11/2013 | Reddy et al. |
| 2013/0331355 | A1 | 12/2013 | Griffith et al. |
| 2013/0345172 | A1 | 12/2013 | Hirst et al. |
| 2014/0194284 | A1 | 7/2014 | Reddy et al. |
| 2014/0194381 | A1 | 7/2014 | Reddy et al. |
| 2014/0194386 | A1 | 7/2014 | Burns et al. |
| 2014/0206648 | A1 | 7/2014 | Reddy et al. |

FOREIGN PATENT DOCUMENTS

| | | |
|---|---|---|
| EP | 1550657 A1 | 7/2005 |
| JP | 2003-229277 | 8/2003 |
| JP | 2004-291253 | 10/2004 |
| WO | WO 87/05297 | 9/1987 |
| WO | WO 89/10961 | 11/1989 |
| WO | WO 98/56392 A1 | 12/1998 |
| WO | WO 00/35904 A1 | 6/2000 |
| WO | WO 00/35905 A1 | 6/2000 |
| WO | WO 01/23374 A1 | 4/2001 |
| WO | WO 01/30149 | 5/2001 |
| WO | WO 02/22137 A1 | 3/2002 |
| WO | WO 02/083884 | 10/2002 |
| WO | WO 03/070714 | 8/2003 |
| WO | WO 2004/039859 | 5/2004 |
| WO | WO 2004/058679 A2 | 7/2004 |
| WO | WO 2004/064755 A2 | 8/2004 |
| WO | WO 2005/033090 | 4/2005 |
| WO | WO 2005/035532 A1 | 4/2005 |
| WO | WO 2005/087700 | 9/2005 |
| WO | WO 2006/091771 | 8/2006 |

(Continued)

OTHER PUBLICATIONS

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

(Continued)

*Primary Examiner* — Kendra D Carter

(74) *Attorney, Agent, or Firm* — Knobbe Martens Olson & Bear LLP

(57) ABSTRACT

Disclosed herein are antimicrobial compounds compositions, pharmaceutical compositions, the use and preparation thereof. Some embodiments relate to boronic acid derivatives and their use as therapeutic agents.

44 Claims, No Drawings

(56) References Cited

FOREIGN PATENT DOCUMENTS

| | | |
|---|---|---|
| WO | WO 2007/058602 A2 | 5/2007 |
| WO | WO 2007/065288 A2 | 6/2007 |
| WO | WO 2007/095638 | 8/2007 |
| WO | WO 2008/039420 A2 | 4/2008 |
| WO | WO 2008/116813 A1 | 10/2008 |
| WO | WO 2009/046098 A1 | 4/2009 |
| WO | WO 2009/064413 A1 | 5/2009 |
| WO | WO 2009/064414 A1 | 5/2009 |
| WO | WO 2009/091856 A1 | 7/2009 |
| WO | WO 2009/117540 A1 | 9/2009 |
| WO | WO 2009/139834 A1 | 11/2009 |
| WO | WO 2009/140309 A2 | 11/2009 |
| WO | WO 2010/056827 A1 | 5/2010 |
| WO | WO 2010/075286 A1 | 7/2010 |
| WO | WO 2010/097675 A1 | 9/2010 |
| WO | WO 2010/130708 A1 | 11/2010 |
| WO | WO 2010/144338 A1 | 12/2010 |
| WO | WO 2011/017125 A1 | 2/2011 |
| WO | WO 2011/103686 A1 | 9/2011 |
| WO | WO 2012/021455 A1 | 2/2012 |
| WO | WO 2012/067664 A1 | 5/2012 |
| WO | WO 2012/106995 A1 | 8/2012 |
| WO | WO 2013/033461 A1 | 3/2013 |
| WO | WO 2013/053372 A1 | 4/2013 |
| WO | WO 2013/056163 A1 | 4/2013 |
| WO | WO 2013/092979 A1 | 6/2013 |
| WO | WO 2013/122888 A2 | 8/2013 |
| WO | WO 2014/089365 A1 | 6/2014 |
| WO | WO 2014/151958 A1 | 9/2014 |

OTHER PUBLICATIONS

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.
Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.
Allen et al., "Ansel's Pharmaceutical Dosage Forms and Drug Delivery Systems", 8th Edition (2004) TOC only.
Arya et al., "Advances in asymmetric enolate methodology", Tetrahedron (2000) 56:917-947.
Babic et al., "What's new in antibiotic resistance? Focus on beta-lactamases", Drug Res Updates (2006) 9:142-156.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Biedrzycki et al., "Derivatives of tetrahedral boronic acids", J. Organomet. Chem. (1992) 431:255-270.
Bou et al., "Cloning, nucleotide sequencing, and analysis of the gene encoding an AmpC beta-lactamase in *Acinetobacter baumannii*", Antimicrob Agents Chemother (2000) 44(2):428-432.
Bou et al., "OXA-24, a novel class D beta-lactamase with carbapenemase activity in an *Acinetobacter baumannii* clinical strain", Antimicrob Agents Chemother. (2000) 44(6):1556-1561 and Erratum in Antimicrob Agents Chemother. (2006) 50(6) 2280.
Brabez et al., "Design,synthesis, and biological studies of efficient multivalent melanotropin ligands: tools toward melanoma diagnosis and treament", J Med Chem. (2011) 54(20):7375-7384.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Bush et al., "Minireview: Updated Functional Classification of beta-Lactamases," Antimicrob Agents Chemo. (2010) 54(3):969-976.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.

Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Coppa et al., "A Facile, Convenient and Selective Homolytic Carbamoylation of Heteroaromatic Bases", Heterocycles (1993) 36(12):2687-2696.
Coutts et al., "Two Efficient Methods for the Cleavage of Pinanediol Boronate Esters Yielding the Free Boronic Acids", Tetrahedron Ltt. (1994) 35(29):5109-5112.
Darses et al., "Potassium Organotrifluoroborates: New Perspectives in organic Synthesis", Chem Rev. (2008) 108:288-325.
Davoli et al., "Enantioselective total synthesis of (-)-microcarpalide", Tetrahedron (2005) 61:4427-4436.
Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.
Endo et al., "Chemoselective Suzuki coupling of diborylmethane for facile synthesis of benzylboronates", Org Lett. (2011) 13(13):3368-3371.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Fan, et al. (2009): STN International HCAPLUS database, Columbus (OH), accession No. 2009: 425839; 6 pages.
Farquhar et al., "Intensely potent doxorubicin analogues: structure—activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Hama et al., "Palladium-Catalyzed alpha-Arylation of Zinc Enolates of Esters: Reaction Conditions and Substrate Scope", J Org Chem. (2013) 78(17):8250-8266.
Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.
Inglis et al., "Observations on the Deprotection of Pinanediol andPpinacol Boronate Esters via Fluorinated Intermediates", J Org Chem. (2010) 75(2):468-471.
Ishii et al, "In vitro potentiation of carbapenems with ME1071, a Novel metallo-β-lactamase inhibitor, against metallo-β-lactamase producing *Pseudomonas aeruginosa* clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]- boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.

(56) References Cited

OTHER PUBLICATIONS

Jiang et al., "A Practical Synthesis of Cefcapene Pivoxil", Synthesis (2012) 44:207-214.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", (1993) 22(5):845-848.
Kint et al., "New-found fundamentals of bacterial persistance", Trends Microbiol. (2012) 20(12):577-585.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kumar et al., "Synthesis of intermediates for the lactone moiety of mevinic acids via tellurium chemistry", J. Org. Chem., (1994) 59(17):4760-4764.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Laitar et al., "Catalytic diboration of aldehydes via insertion into the copper-boron bond", J Am Chem Soc. (2006) 128(34):11036-11037.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.
Liu et al., "Selective Protein tyrosine phosphatase 1B inhibitors: Targeting the second phosphotyrosine binding site with non-carboxylic acid-containing ligands", J Med Chem. (2003) 46(16):3437-3440.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.
Matteson et al., "Synthesis of a (Beta-acetamido-alpha-acetoxyethyl) boronic ester via azido boronic esters", J Organomet Chem. (2008) 693:2258-2262.

Meanwell, "Synopsis of some recent tactical application of bioisosteres in drug design", J. Med. Chem. (2011) 54:2529-2591.
Micalizio et al., "A Boronic Ester Annulation Strategy for Diversity-Oriented Organic Synthesis", Angew Chem Int Ed Engl. (2002) 41(1):152-154.
Montalbetti et al., "Amide bond formation and peptide coupling", Tetrahedron (2005) 61:10827-10852.
Montefour et al., "*Acinetobacter baumannii*: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Nema et al., "Excipients and Their Role in Approved Injectable Products: Current Usage and Future Directions", PDA J Pharm Sci Technol. (2011) 65(3):287-332.
Ness et al., "Structure-based design guides the improved efficacy of deacylation transition state analogue inhibitors of TEM-1 beta-Lactamase", Biochemistry (2000) 39(18):5312-5321.
Nordmann et al., How to Detect NDM-1 Producers, J. Clin. Micro. (2011) 49:718-721.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paterson et al., "Extended-Spectrum beta-Lactamases: a Clinical Update", Clin Microbiol Rev. (2005) 18(4):657-686.
Perez et al., "Why are we afraid of *Acinetobacter baumannii*?", Expert Rev Anti Infect Ther. (2008) 6(3):269-71.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.
Powell et al., "Compendium of excipients for parenteral formulations", PDA J Pharm Sci Technol. (1998) 52(5):238-311.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Robak et al., "Synthesis and applications of tert-butanesulfinamide", Chem Rev. (2010) 110(6):3600-3740.
Rodriguez-Martinez et al., "VIM-19, a Metallo-beta-lactamase with increased Carbapenemase Activity from *Escherichia coli* and *Klebsiella pneumoniae*", Antimicro Agents Chemother. (2010) 54(1):471-476.
Sawyer et al., "Physical properties and synthetic utility of a-alkoxyorganolithium species as studied through ligand selectivity in tin-lithium exchange", J. Am. Chem. Soc. (1988) 110:842-853.
Selander et al., "Palladium-catalyzed allylic C-OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: a short step asymmetric synthesis of 6-substituted 5,6-dehydro-2-pyrones", Tetrahedron (1993) 49(10):1997-2010.
Singh et al., "Assymetric Homologation of Boronic Esters Bearing Azido and Silyloxy Substituents", J Org Chem (2000) 65(20):6650-6653 and Erratum: J Org Chem. (2001) 66(22):7560.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3$S$,5$R$,7$R$,10$R$,11$R$)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C—H insertion", Tetrahedron (2002) 58:6545-6554.

(56) References Cited

OTHER PUBLICATIONS

Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Vasil'ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Waley, Stephen G., "A quick method for the determination of inhibition constants", Biochem J. (1982) 205(3):631-633.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Wohlrab et al., "Total synthesis of plusbacin A3: a depsipeptide antibiotic active against vancomycin-resistant bacteria", J. Am. Chem. Soc. (2007) 129:4175-4177.
Xia et al., "Synthesis and SAR of novel benzoxaboroles as a new class of beta-lactamase inhibitors", Bioorg Med Chem Lett. (2011) 21:2533-2536.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005)46(46):7899-7903.
International Search Report and Written Opinion dated Sep. 14, 2011 for International Patent Application No. PCT/US2011/046957, filed Aug. 8, 2011.
International Search Report and Written Opinion dated Nov. 5, 2012 for International Patent Application No. PCT/US2012/053233, filed Aug. 30, 2012.
International Search Report and Written Opinion dated May 9, 2013 for International Patent Application No. PCT/US2013/025621, filed Feb. 11, 2013.
International Search Report and Written Opinion dated Aug. 29, 2013 for International Application No. PCT/US2013/044377, filed Jun. 5, 2013.
International Search Report and Written Opinion dated Mar. 12, 2014 for International Patent Application No. PCT/US2014/010106, filed Jan. 2, 2014.
International Search Report and Written Opinion dated Mar. 12, 2014 for International Patent Application No. PCT/US2014/010107, filed Jan. 2, 2014.
U.S. Office Action, mailed Aug. 20, 2013, in U.S. Appl. No. 13/205,112.
U.S. Office Action, mailed Apr. 1, 2014, in U.S. Appl. No. 13/898,959.
Chemicalland21.com. "Meglumine", Jun. 7, 2011. Downloaded from </www.chemicalland21.com/lifescience/phar/N-METHYL-D-GLUCAMINE.htm>; 2 pages.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
U.S. Office Action mailed Oct. 3, 2014 in U.S. Appl. No. 14/146,671.

BORONIC ACID DERIVATIVES AND THERAPEUTIC USES THEREOF

CROSS-REFERENCE TO RELATED APPLICATIONS

This application claims the benefit of U.S. Provisional Application No. 61/749,210, filed Jan. 4, 2013, which is incorporated herein by reference in its entirety.

BACKGROUND

1. Field of the Invention

The present invention relates to the fields of chemistry and medicine. More particularly, the present invention relates to boronic acid antimicrobial compounds, compositions, their preparation, and their use as therapeutic agents.

2. Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other Enterobacteriaceae, *Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved β-lactamase inhibitors.

SUMMARY

Some embodiments disclosed herein include a compound having the structure of formula I:

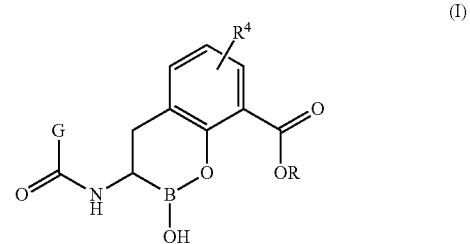

(I)

or pharmaceutically acceptable salt thereof, wherein:

G is selected from the group consisting of —H, —NR$^1$R$^2$, —CH$_2$N$_3$, —C(O)NR$^1$R$^2$, —CH$_2$C(O)NR$^1$R$^2$, —CH$_2$S(O)$_2$NR$^1$R$^2$, —CH$_2$—Y—Z, —CH$_2$—Y—X, and —SR$^3$;

Y is selected from a group consisting of —S—, —S(O)—, —S(O)$_2$—, —O—, and —NR$^1$—;

R is selected from a group consisting of —H, —C$_{1-9}$alkyl, —CR$^1$R$^2$OC(O)C$_{1-9}$alkyl, —CR$^1$R$^2$OC(O)OC$_{1-9}$alkyl, and

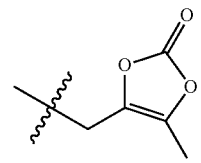 [SMILES: *Cc1oc(=O)oc1C]

R$^1$ and R$^2$ are each independently selected from the group consisting of —H and —C$_{1-4}$alkyl;

R$^3$ is —C$_{1-4}$alkyl;

R$^4$ is present 1 to 3 times and each R$^4$ is independently selected from the group consisting of —H, —C$_{1-4}$alkyl, —OH, —OC$_{1-4}$alkyl, and halogen;

Z is selected from the group consisting of aryl optionally substituted with C$_{1-4}$alkyl, amino, hydroxy, or halogen and heteroaryl optionally substituted with $C_{1-4}$alkyl, amino, hydroxy, or halogen;

X is selected from the group consisting of —$C_{1-4}$alkyl, —$CH_2R^5$, —$CH(R^5)_2$, and —$C(R^5)_3$; and $R^5$ is selected from the group consisting of a halogen, cyano, and azido group.

Some embodiments disclosed herein include a compound having the structure of formula II:

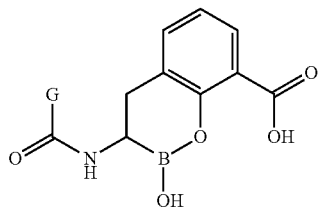

or pharmaceutically acceptable salt thereof, wherein:

G is selected from the group consisting of

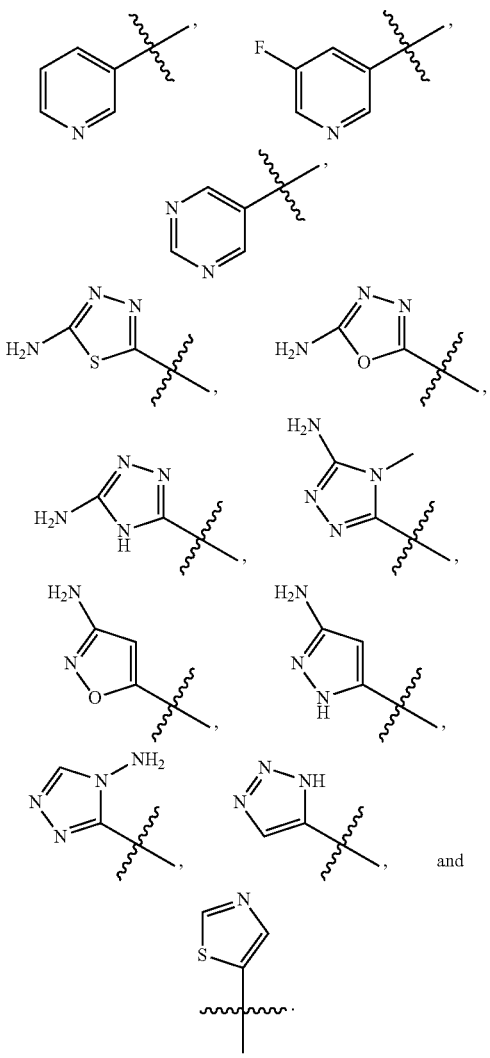

and

Other embodiments disclosed herein include a pharmaceutical composition comprising a therapeutically effective amount of a compound disclosed herein and a pharmaceutically acceptable excipient.

Other embodiments disclosed herein include a method of treating or preventing a bacterial infection, comprising administering to a subject in need thereof a compound disclosed herein.

DETAILED DESCRIPTION

In some embodiments, compounds that contain a boronic acid moiety are provided that act as antimicrobial agents and/or as potentiators of antimicrobial agents Various embodiments of these compounds include compounds having the structures of Formulas I and Ia as described above or pharmaceutically acceptable salts thereof.

Some embodiments of compounds of Formula (I) or their pharmaceutically acceptable salts have the following stereochemistry as shown in the structure of formula (Ia):

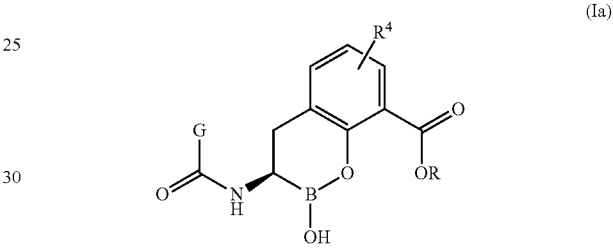

In some embodiments, R in any of the preceding compounds is H.

In some embodiments, $R^4$ may be either ortho, para, or meta to the carboxylic acid moiety of the phenyl ring. In some embodiments, $R^4$ in any of the preceding compounds is H.

In some embodiments, G in any of the preceding compounds is H.

In some embodiments, G in any of the preceding compounds is $NH_2$.

In some embodiments, G in any of the preceding compounds is —$C(O)NR^1R^2$ and $R^1$ and $R^2$ are each independently selected from —H and $C_{1-4}$alkyl. In some such embodiments, $R^1$ is $CH_3$ and $R^2$ is $CH_3$.

In some embodiments, G is —$CH_2C(O)NR^1R^2$ and $R^1$ and $R^2$ are each independently selected from —H and $C_{1-4}$alkyl. In some such embodiments, $R^1$ is $CH_3$ and $R^2$ is $CH_3$.

In some embodiments, $R^3$ in any of the preceding compounds is $CH_3$.

In some embodiments, G is $CH_2$—Y—Z; Y is —S—; and Z is selected from the group consisting of imidazole, N-methylimidazole, aminoimidazole, triazole, N-methyl triazole, aminotriazole, tetrazole, N-methyltetrazole, aminotetrazole, thiazole, aminothiazole, thiadiazole, aminothiadiazole, oxazole, oxadiazole, pyridine, pyridazine, pyrimidine and pyrazine. In some such embodiments, Z is N-methyltetrazole. In other embodiments, Z is thiadiazole. In other embodiments, Z is aminothiadiazole.

In some embodiments, G is $CH_2$—X and Y is —S—. In some such embodiments, X is $CH_3$. In other embodiments, X is $CH_2CN$. In other embodiments, X is —$CH_2F$. In other embodiments, X is X is —$CHF_2$. In some embodiments, X is —$CF_3$.

Some specific embodiments of the compounds described herein have the following structures:

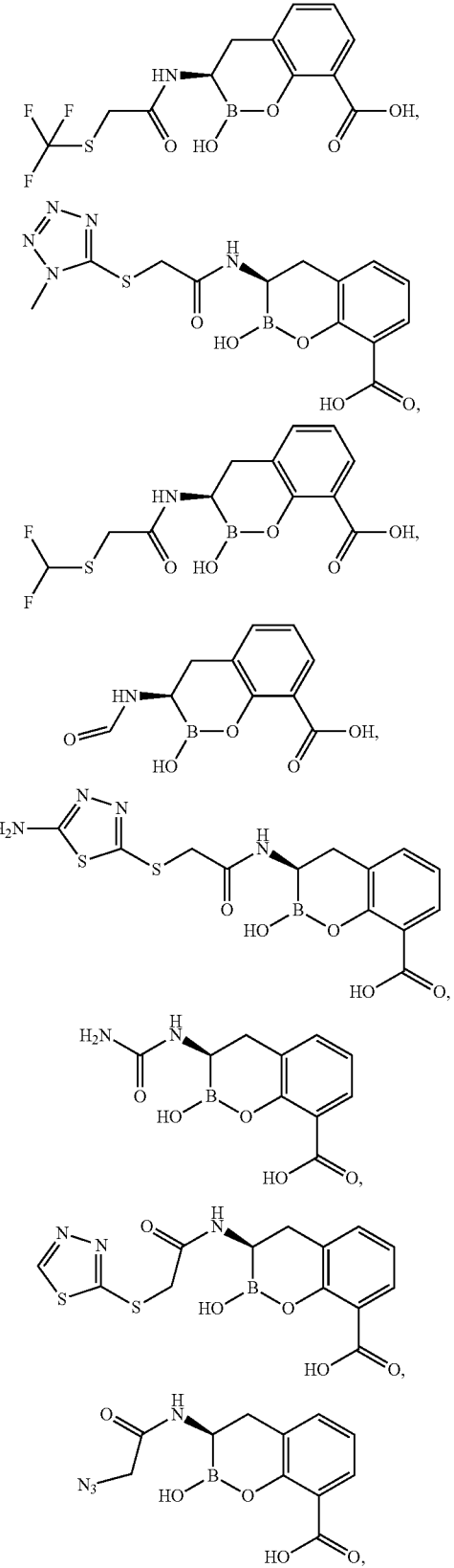

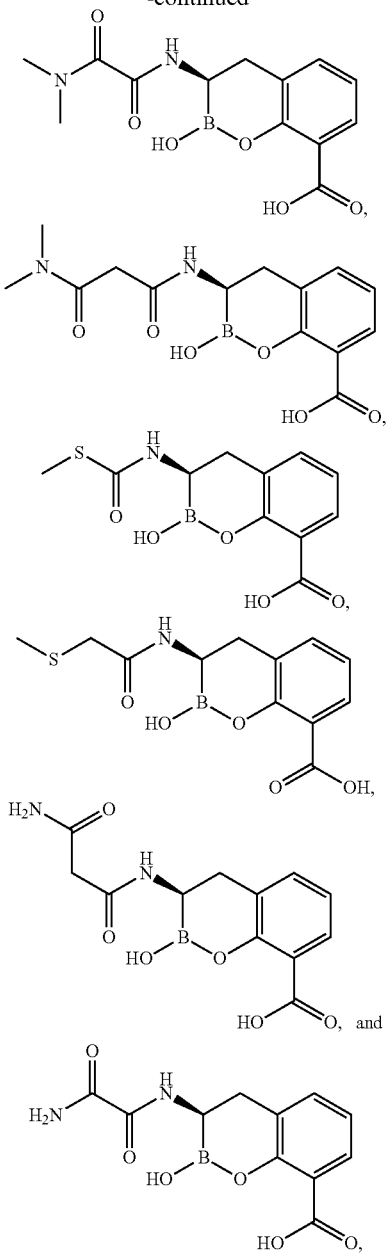

or pharmaceutically acceptable salts thereof.

Some embodiments of compounds of Formula (II) or their pharmaceutically acceptable salts have the following stereochemistry as shown in the structure of formula (IIa):

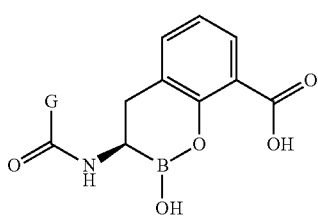

(IIa)

Some specific embodiments of the compounds described herein have the following structures:

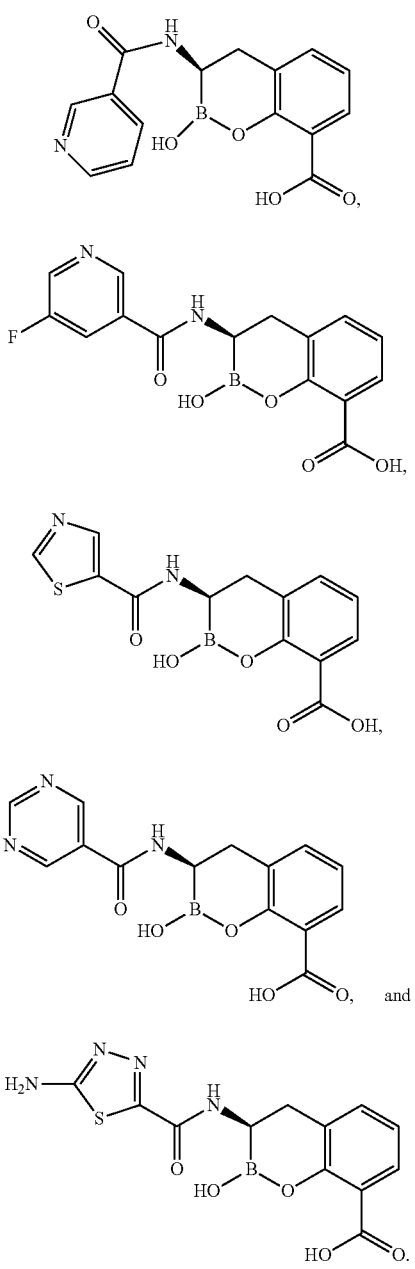

or pharmaceutically acceptable salts thereof.

Some embodiments of any of the compounds described above include prodrugs (e.g., prodrug esters), metabolites, stereoisomers, hydrates, solvates, polymorphs, and pharmaceutically acceptable salts of those compounds.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As shown below, the compounds disclosed herein may exist in cyclic form as cyclic boronate monoesters as formula I (or II) or in acyclic form as boronic acids as formula I.1 (or II.1) (*Biochemistry*, 2000, 39, 5312-21), or may exist as a mixture of the two forms depending on the medium. Such compounds or mixture of compounds are considered within the scope of the structures depicted, though such structural forms are not explicitly represented herein.

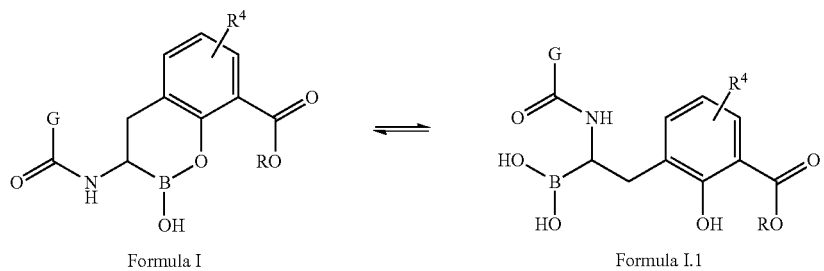

Formula I              Formula I.1

DEFINITIONS

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and Rb are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)). Handling of protecting and/or sterodirecting groups specific to boronic acid derivatives is described in a recent review of chemistry of boronic acids: D. G. Hall (Ed.), Boronic Acids. Preparation and Application in Organic Synthesis and Medicine, Wiley VCH (2005) and in earlier reviews: Matteson, D. S. (1988). Asymmetric synthesis with boronic esters. Accounts of Chemical Research, 21(8), 294-300, and Matteson, D. S. (1989). Tetrahedron, 45(7), 1859-1885), all of which are incorporated herein by reference in their entirety. The latter review articles also describe methodology for stereoselective insertion of halomethine functionality next to the boronate which is employed in the synthetic schemes below.

In addition to standard acid catalyzed deprotection, special methods for removal of boronic acid protecting and/or sterodirecting groups methods using fluorides (Yuen, A. K. L., & Hutton, C. A. (2005). Tetrahedron Letters, 46(46), 7899-7903—incorporated herein by reference in its entirety) or periodate oxidation (Coutts, S. J., et al. (1994). Tetrahedron Letters, 35(29), 5109-5112—incorporated herein by reference in its entirety) can also be employed in preparations of the compounds disclosed herein.

In strategies employing pinanediol or other diol-based chiral auxiliaries for stereospecific introduction of new chiral centers, the early stages of chemistry on boronic intermediates can be performed on chiral boronate esters or alternatively nonchiral borate/boronate intermediates can be used in early stages followed by transesterification with chiral diols prior to the step where stereoselection is required.

Synthesis of Compounds of Formula I

Compounds of formula I where R is H can be prepared as depicted in scheme 1 from intermediates of formula III, which may be assembled by several known α-aminoboronate formation reactions (Boronic Acids: Preparations and Applications in Organic Synthesis, Medicine and Materials, D. G. Hall, ed., Wiley-VCH, Weinheim, 2011, which is incorporated herein by reference in its entirety).

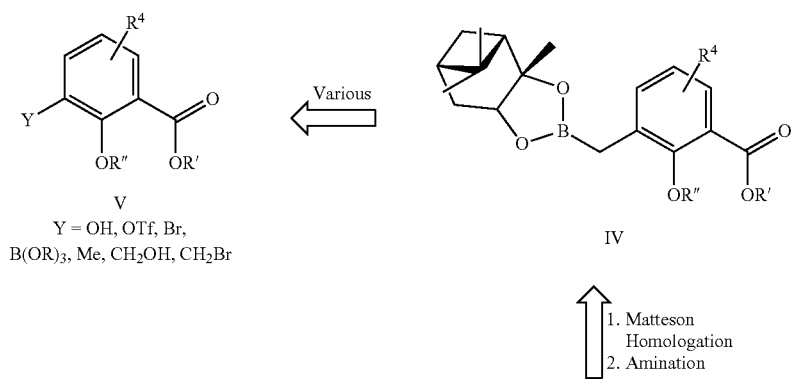

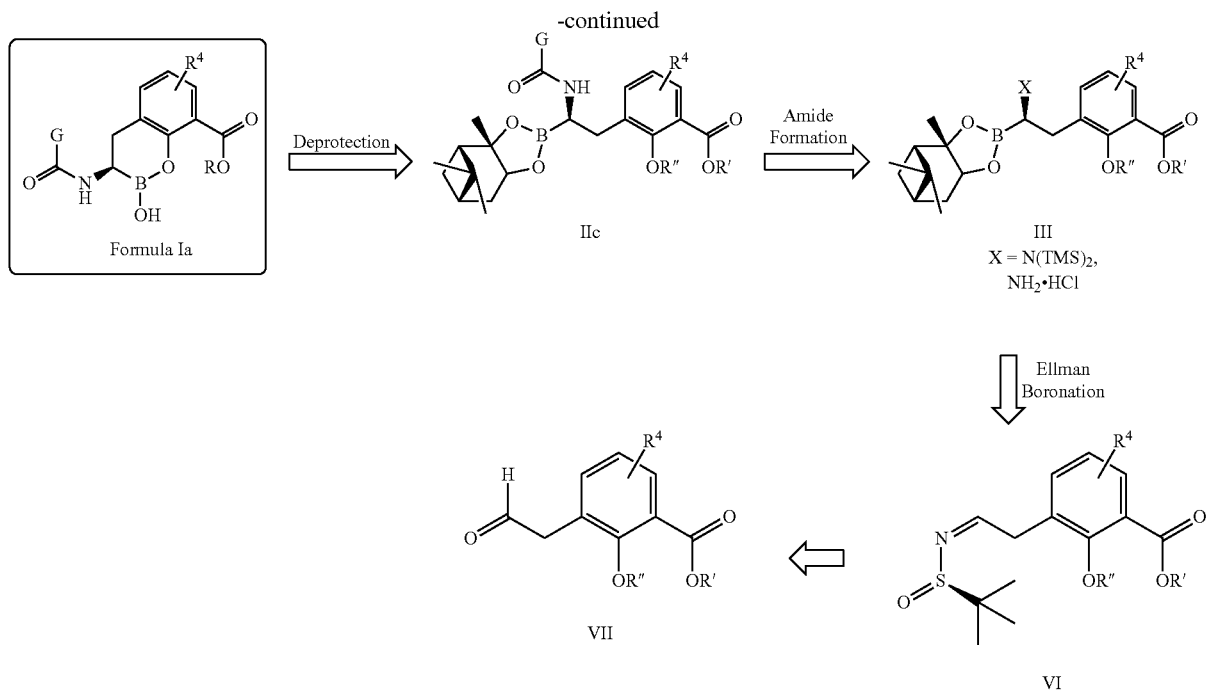

Such intermediates of formula III where X=—N(TMS)$_2$ and R' and R" are alkyl groups may be prepared by earlier described methods (PCT Publication Nos. WO09064414 and WO10130708, which are incorporated herein by reference in their entirety). In an alternate sequence, compounds of formula III, where X=—N(TMS)$_2$ and R" is Boc and R' is t-Butyl or R' and R" are protected together as isopropylidene or any other groups protected separately or together in cyclic form, may be made from compounds of formula IV via homologation to give chloromethylene addition product with good stereocontrol by Matteson reaction conditions, followed by stereospecific substitution with hexamethyldisilazane (PCT Publication No. WO0946098, which is incorporated herein by reference in its entirety). Bromo precursors may be made analogously to the chloro compounds utilizing dibromomethane (J. Am. Chem. Soc. 1990, 112, 3964-969, which is incorporated herein by reference in its entirety). Matteson reaction precursors of formula IV may be made by palladium mediated coupling of pinanediol diboronate from corresponding appropriately protected benzyl alcohols (J. Am. Chem. Soc. 2011, 133, 409-411, which is incorporated herein by reference in its entirety) or benzyl bromides V (Tetrahedron Letters 2003, 44, 233-235; J. Am. Chem. Soc., 2010, 132, 11825-11827, which is incorporated herein by reference in its entirety). Compounds of formula IV may also be prepared by homologation of the corresponding arylboronate ester by reaction with chloromethyl anion (PCT Publication No. WO09064414, which is incorporated herein by reference in its entirety). The compounds of formula V may be achieved by means of several earlier known methods (PCT Publication No. WO0458679, which is incorporated herein by reference in its entirety) with conventional protecting groups, such as those described in *Protective Groups in Organic Chemistry* (ed. J. F. W. McOmie, Plenum, 1973); and *Protecting Groups in Organic Synthesis*, P. G. M. Wutts, T. W. Green, Wiley, New York, 1999) (both incorporated herein by reference in their entirety) from commercially available salicylic acid derivatives. Compounds of formula V where Y is methyl can be readily transformed to corresponding benzyl bromides (Bioorg. Med. Chem. Lett. 1999, 9, 34-346, which is incorporated herein by reference in its entirety) for boronation reaction to give IV.

Bis-trimethyl silylamides of formula III may be reacted in situ with an acid chloride to result directly in analogs of formula IIc. Such analogs of IIc can also be made via coupling of the bis-TMS amine with commercially available carboxylic acids under typical amide coupling conditions (e.g., carbodiimide or HATU coupling) (Tetrahedron, 2005, 61, 10827-10852, which is incorporated herein by reference in its entirety). Varieties of substituted thioacetic acid or glycolate or glycinate precursors are commercially available. Such precursors may be also obtained by several well-known methods in the literature (J. Org. Chem. (2012), DOI: 10.1021/jo302088t, which is incorporated herein by reference in its entirety).

Simultaneous deprotection of pinane ester and salicylic acid protective groups of compounds of formula IIc can be achieved by heating with dilute HCl, affording the desired compounds of formula I. This transformation may also be achieved by treatment with BCl$_3$ or BBr$_3$ (PCT Publication No. WO09064414, which is incorporated herein by reference in its entirety). Alternatively, the deprotection may be attained via trans-esterification with isobutyl boronic acid in presence of dilute acid (PCT Publication No. WO09064413, which is incorporated herein by reference in its entirety) or via other known methods (*J. Org. Chem.* (2010), 75, 468-471, which is incorporated herein by reference in its entirety).

In an alternate approach, compounds of formula III where X is NH$_2$.HCl can be made via asymmetric addition of boron to a carbon heteroatom double bond, enabling production of enantiomerically pure N-sulfinyl-α-amino boronate ester derivatives. Such transformation is achieved form appropriately protected N-sulfinyl imine (VI) using a Cu/ligand catalyst system (*J. Am. Chem. Soc.* (2008), 130, 6910-6911, which is incorporated herein by reference in its entirety) followed by treatment with mild acid. Enantiomerically pure N-sulfinyl imines of formula VI may be made by condensation of appropriately protected phenylacetaldehyde intermediates (VII) and enantiomerically pure t-butylsulfonylamine (*Chem. Rev.* 2010, 110, 3600-3740, which is incorporated herein by reference in its entirety).

Phenylacetaldehyde derivatives of formula VII can be made from Claisen rearrangement of allyl ethers of commercially available salicylates followed by oxidative cleavage of the allyl group (*J. Med. Chem.* 1995, 38, 3094-3105, which is incorporated herein by reference in its entirety). Such intermediates of formula VII can also be made by Wacker oxidation of vinyl substituted salicylates (*Org. Lett.* 2012, 14, 3237-3239, which is incorporated herein by reference in its entirety). Protective groups may be used separately for phenol and acid or together from a variety of available options as described above.

Synthesis of Prodrugs

Compounds of formula I where the R is a prodrug moiety may be synthesized by a variety of known methods of different carboxylic acid prodrugs (*Prodrugs: Challenges and Rewards*, V. J. Stella, et al., ed., Springer, New York, 2007, which is incorporated herein by reference in its entirety). These prodrugs include but are not limited to substituted or non-substituted alkyl esters, (acyloxy)alkyl esters (*Synthesis* 2012, 44, 207, which is incorporated herein by reference in its entirety), [(alkoxycarbonyl)oxy]methyl esters (PCT Publication No. WO10097675, which is incorporated herein by reference in its entirety), or (oxodioxolyl)methyl esters (*J. Med. Chem.* 1996, 39, 323-338, which is incorporated herein by reference in its entirety). Such prodrugs can be made from compounds of formula I where R═H by treatment with acid or in neutral conditions (e.g., carbodiimide coupling) in the presence of alcohols (ROH) or via base promoted esterification with RX where X is a leaving group in the presence of an appropriate base. Alternatively, compounds of formula VIII may be also utilized for introduction of prodrugs (Scheme 2). Such carboxylic acids (VIII) can be made from compounds of formula II by selective deprotection of OR'. The prodrug group may also be introduced earlier in the sequence in compounds of formula V or VII where R' is R. Such a sequence where the prodrug is introduced in earlier intermediates is only feasible when the ester is stable under the final deprotection conditions to remove the phenol protective group and the boronate ester.

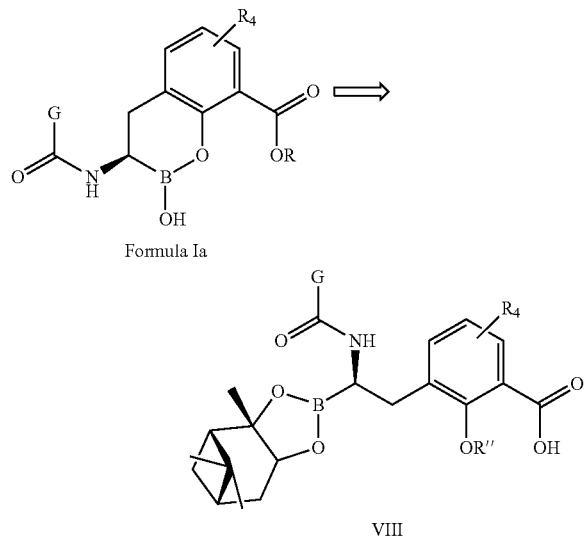

Scheme 2

Formula Ia

VIII

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, come embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with the compounds and compositions comprising the compounds described herein. Some methods include administering a compound, composition, pharmaceutical composition described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Examples of additional medicaments include an antibacterial agent, antifungal agent, an antiviral agent, an anti-inflammatory agent and an anti-allergic agent.

Preferred embodiments include combinations of a compound, composition or pharmaceutical composition described herein with an antibacterial agent such as a β-lactam. Examples of such β-lactams include Amoxicillin, Ampicillin (e.g., Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Preferred embodiments include β-lactams such as Ceftazidime, Biapenem, Doripenem, Ertapenem, Imipenem, Meropenem and Panipenem.

Additional preferred embodiments include β-lactams such as Aztreonam, Tigemonam, and Carumonam.

Some embodiments include a combination of the compounds, compositions and/or pharmaceutical compositions described herein with an additional agent, wherein the additional agent comprises a monobactam. Examples of monobactams include aztreonam, tigemonam, nocardicin A, carumonam, and tabtoxin. In some such embodiments, the compound, composition and/or pharmaceutical composition comprises a class A, C, or D beta-lactamase inhibitor. Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises a class B beta lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Some embodiments include co-administering the compound, composition or pharmaceutical composition described herein with one or more additional agents.

Some embodiments include a combination of the compounds, compositions and/or pharmaceutical compositions described herein with an additional agent, wherein the additional agent comprises one or more agents that include a class A, B, C, or D beta lactamase inhibitor. Some embodiments include co-administering the compound, composition or pharmaceutical composition described herein with the one or more additional agents.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtherias, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

The following examples will further describe the present invention, and are used for the purposes of illustration only, and should not be considered as limiting.

EXAMPLES

Example 1

(R)-2-hydroxy-3-(2-(trifluoromethylthio)acetamido)-3,4-dihydro-2H-benzo[e][1,2]oxaborinine-8-carboxylic acid (1)

Scheme 3:

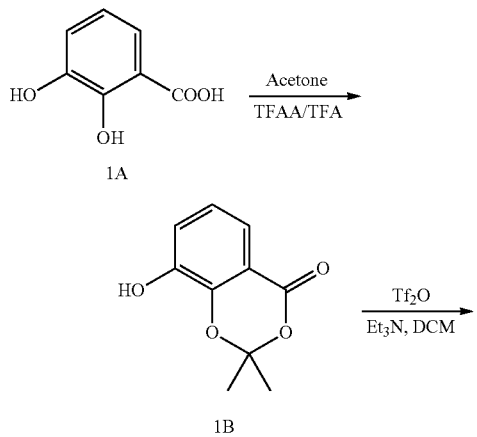

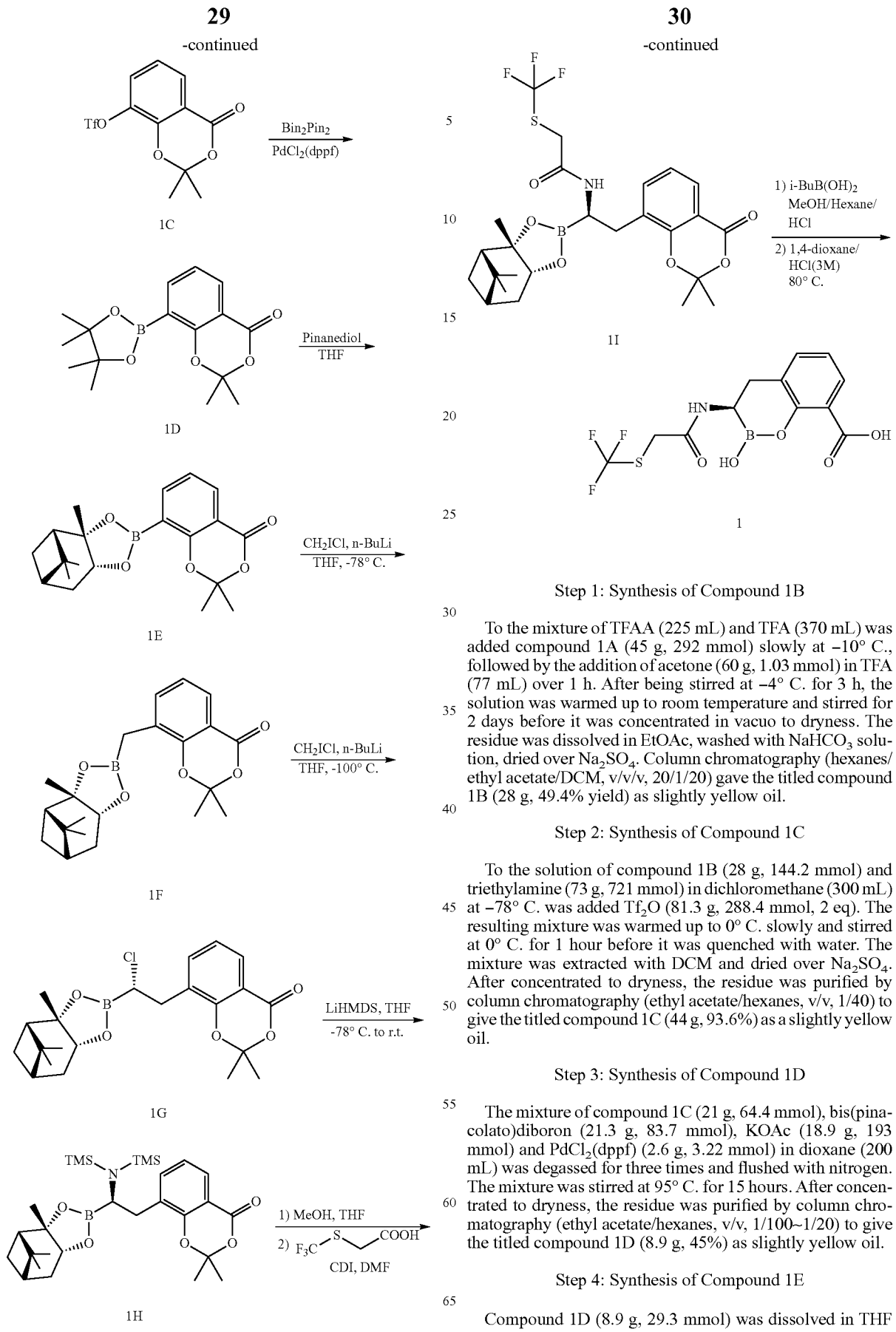

Step 1: Synthesis of Compound 1B

To the mixture of TFAA (225 mL) and TFA (370 mL) was added compound 1A (45 g, 292 mmol) slowly at −10° C., followed by the addition of acetone (60 g, 1.03 mmol) in TFA (77 mL) over 1 h. After being stirred at −4° C. for 3 h, the solution was warmed up to room temperature and stirred for 2 days before it was concentrated in vacuo to dryness. The residue was dissolved in EtOAc, washed with NaHCO$_3$ solution, dried over Na$_2$SO$_4$. Column chromatography (hexanes/ ethyl acetate/DCM, v/v/v, 20/1/20) gave the titled compound 1B (28 g, 49.4% yield) as slightly yellow oil.

Step 2: Synthesis of Compound 1C

To the solution of compound 1B (28 g, 144.2 mmol) and triethylamine (73 g, 721 mmol) in dichloromethane (300 mL) at −78° C. was added Tf$_2$O (81.3 g, 288.4 mmol, 2 eq). The resulting mixture was warmed up to 0° C. slowly and stirred at 0° C. for 1 hour before it was quenched with water. The mixture was extracted with DCM and dried over Na$_2$SO$_4$. After concentrated to dryness, the residue was purified by column chromatography (ethyl acetate/hexanes, v/v, 1/40) to give the titled compound 1C (44 g, 93.6%) as a slightly yellow oil.

Step 3: Synthesis of Compound 1D

The mixture of compound 1C (21 g, 64.4 mmol), bis(pinacolato)diboron (21.3 g, 83.7 mmol), KOAc (18.9 g, 193 mmol) and PdCl$_2$(dppf) (2.6 g, 3.22 mmol) in dioxane (200 mL) was degassed for three times and flushed with nitrogen. The mixture was stirred at 95° C. for 15 hours. After concentrated to dryness, the residue was purified by column chromatography (ethyl acetate/hexanes, v/v, 1/100~1/20) to give the titled compound 1D (8.9 g, 45%) as slightly yellow oil.

Step 4: Synthesis of Compound 1E

Compound 1D (8.9 g, 29.3 mmol) was dissolved in THF (100 mL) and (+)-pinanediol (4.98 g, 29.3 mmol) was added.

The resulting reaction mixture was stirred at room temperature for 15 hours. After concentrated to dryness, the residue was purified by column chromatography (ethyl acetate/hexanes, v/v, 1/200~1/50) to give the titled compound 1E (3.2 g, 31% yield) as slightly yellow oil.

MS calcd for ($C_{20}H_{25}BO_5$): 356
MS (ESI, positive) found: (M+1): 357

Step 5: Synthesis of Compound 1F

To a solution of $CH_2ICl$ (1.34 g, 7.67 mmol) in THF (15 mL) at −78° C. was added 2.5 M n-butyl lithium in hexane (3.07 mL, 7.67 mmol) slowly under nitrogen and down the inside wall of the flask. The resulting solution was stirred for 30 minutes before the addition of Compound 1E from step 4 (2.1 g, 5.90 mmol) in THF (5 mL) at −78° C. The reaction was allowed to warm to room temperature and stirred for 16 h before it was quenched with a saturated solution of ammonium chloride. The phases were separated. The aqueous phase was extracted with diethyl ether (3×50 mL) and the combined organic extracts were dried over $Na_2SO_4$. The concentrated material was chromatographed (100% hexane-20% EtOAc-hexane) to obtain the titled compound 1F (2.07 g, 95% yield) as slightly yellow oil.

MS calcd for ($C_{21}H_{27}BO_5$): 370
MS (ESI, positive) found: (M+1): 371

Step 6: Synthesis of Compound 1G

To a solution of $CH_2Cl_2$ (0.72 mL, 11.2 mmol) in THF (20 mL) at −100° C. was added 2.5 M n-butyl lithium in hexane (2.9 mL, 7.28 mmol) slowly under nitrogen and down the inside wall of the flask, maintaining the temperature below −90° C. The reaction mixture was stirred for 30 minutes before the addition of Compound 1F from step 5 (2.07 g, 5.6 mmol) in THF (5 mL) at −90° C. The reaction was allowed to warm to room temperature slowly and stirred at room temperature for 16 h. The reaction mixture was quenched with a saturated solution of ammonium chloride and the phases were separated. The aqueous phase was extracted with diethyl ether (3×50 mL) and the combined organic extracts were dried over $Na_2SO_4$, filtered and concentrated under reduced pressure. The concentrated material was then chromatographed (100% hexane-20% EtOAc-hexane) to obtain the titled compound 1G (1.48 g, 63% yield) as slightly yellow oil.

Step 7: Synthesis of Compound 1H

Compound 1G (1.48 g, 3.53 mmol) in THF (15 mL) was cooled to −78° C. under nitrogen. A solution of 1 M LiHMDS solution in THF (3.6 mL, 3.6 mmol) was added slowly at −78° C. Upon completion of the addition, the reaction flask was allowed to warm to room temperature. After stirring at room temperature for 16 h, the reaction mixture was concentrated under vacuum and hexane (20 mL) was added. The precipitated lithium salts were filtered off through a Celite pad, rinsed with additional hexane and the combined filtrates were concentrated under vacuum to give crude bis(trimethylsilyl) amine product 1H (3.5 mmol).

MS calcd for ($C_{28}H_{46}BNO_5Si_2$): 543
MS (ESI, positive) found: (M−2*TMS+3): 400

Step 8: Synthesis of Compound 1I

Bis(trimethylsilyl)amine compound 1H (260 mg, 0.48 mmol) was stirred in MeOH/THF (1 mL/10 mL) for 30 min at room temperature before it was concentrated to dryness in vacuo to afford the free amine as yellow oil. Trifluoromethylsulfanyl-acetic acid (91 mg, 0.57 mmol) and CDI (115 mg, 0.71 mmol) were dissolved in DMF (2 mL) at stirred at 45° C. for 1 h. After cooling down, the free amine obtained above in 1 mL DMF was added and was stirred at room temperature for 15 hours. The mixture was diluted with DCM and washed with water and brine, dried over $Na_2SO_4$. The concentrated material was then chromatographed (EtOAc-hexane: 1/20~1/2) to obtain the titled compound 1I (110 mg, 42.5% yield) as slightly yellow oil.

MS calcd for ($C_{25}H_{31}BF_3NO_6S$): 541
MS (ESI, negative) found: (M−1): 540

Step 9: Synthesis of (R)-2-hydroxy-3-(2-(trifluoromethylthio)acetamido)-3,4-dihydro-2H-benzo[e][1,2] oxaborinine-8-carboxylic acid (1)

To the solution of compound I (110 mg, 0.2 mmol) in MeOH/hexane (2 mL/2 mL) was added isobutyl boronic acid (41 mg, 0.4 mmol) and concentrated HCl (0.2 mL) at 0° C. The resulting mixture was stirred at room temperature for 1 h. The two layers were separated and the MeOH layer was washed with hexanes twice before it was concentrated in vacuo. The residue was stirred in dioxane (2 mL) and 3 N aqueous HCl (3 mL) at 80° C. for 2 h. After concentration, the residue was purified by reverse-phase prep-HPLC to afford 1 (8 mg) as a white solid after lyophilization.

$^1$H NMR (400 MHz, $CD_3OD$) δ 7.83 (dd, 1H, J=6.0, 6.0 Hz), 7.32 (d, 1H, J=6.8 Hz), 6.96 (dd, 1H, J=8.0, 8.0 Hz), 3.86 (d, 2H, J=5.6 Hz), 3.34 (s, 1H), 2.97 (s, 2H).

MS calcd for ($C_{12}H_{11}BF_3NO_5S$): 349
MS (ESI, positive) found: (M+1): 350
MS (ESI, negative) found: (M−1): 348

Example 2

(R)-2-hydroxy-3-(2-(1-methyl-1H-tetrazol-5-ylthio) acetamido)-3,4-dihydro-2H-benzo[e][1,2]oxaborinine-8-carboxylic acid (2)

Scheme 5:

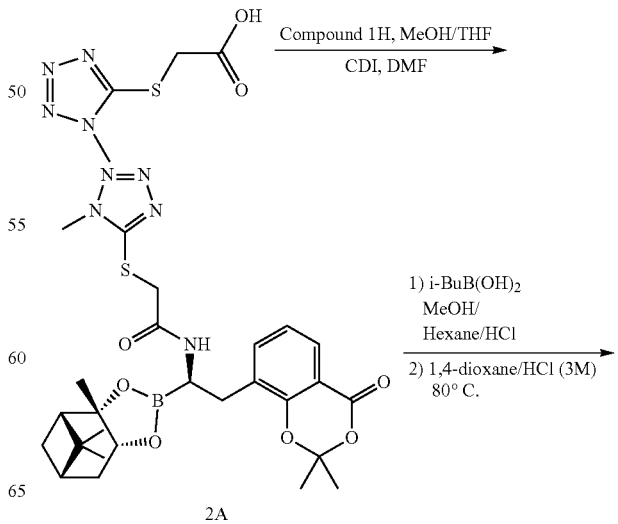

2A

-continued

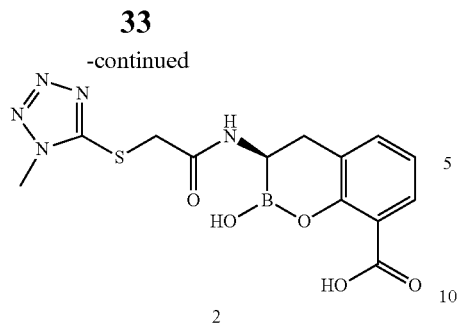

2

Step 1: Synthesis of Compound 2A

Bis(trimethylsilyl)amine compound 1H (260 mg, 0.48 mmol) was stirred in MeOH/THF (1 mL/10 mL) for 1 h at room temperature before it was concentrated to dryness in vacuo to afford the free amine as yellow oil. (1-Methyl-1H-tetrazol-5-ylsulfanyl)-acetic acid (99 mg, 0.57 mmol) and CDI (115 mg, 0.71 mmol) were dissolved in DMF (2 mL) at stirred at 50° C. for 2 h. After cooling down, the free amine obtained above in 1 mL DMF was added and was stirred at room temperature for 15 hours. The mixture was diluted with DCM and washed with water and brine, dried over $Na_2SO_4$. After concentration, the crude compound 2A was used directly for next step (205 mg, crude).

MS calcd for ($C_{26}H_{34}BN_5O_6S$): 555
MS (ESI, negative) found: (M−1): 554

Step 2: Synthesis of (R)-2-hydroxy-3-(2-(1-methyl-1H-tetrazol-5-ylthio)acetamido)-3,4-dihydro-2H-benzo[e][1,2]oxaborinine-8-carboxylic acid (2)

To the solution of compound 2A (200 mg, crude) in MeOH/hexane (1.5 mL/1.5 mL) was added isobutyl boronic acid (82 mg, 0.8 mmol) and concentrated HCl (0.15 mL) at 0° C. The resulting mixture was stirred at room temperature for 1 h. The two layers were separated and the MeOH layer was diluted with 10 mL MeOH, washed with hexanes twice before it was concentrated in vacuo. The residue was stirred in dioxane (1.5 mL) and 3 N aqueous HCl (1.5 mL) at 80° C. for 2 h. After concentration, the residue was purified by reverse-phase prep-HPLC to afford 2 (17 mg) as a white solid after lyophilization.

$^1$H NMR (400 MHz, $CD_3OD$) δ 7.74 (dd, 1H, J=2.0, 8.4 Hz), 7.09 (d, 1H, J=6.4 Hz), 6.81 (t, 1H, J=7.6 Hz), 4.12-4.24 (m, 2H), 3.80 (s, 3H), 3.34 (s, 1H), 2.89 (d, 2H, J=3.6 Hz).
MS calcd for ($C_{13}H_{14}BN_5O_5S$): 363
MS (ESI, positive) found: (M+1): 364
MS (ESI, negative) found: (M−1): 362

Example 3

(R)-3-(2-(difluoromethylthio)acetamido)-2-hydroxy-3,4-dihydro-2H-benzo[e][1,2]oxaborinine-8-carboxylic acid (3)

Scheme 6:

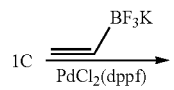

-continued

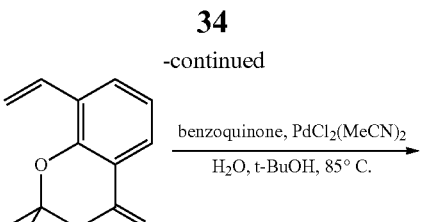
3A

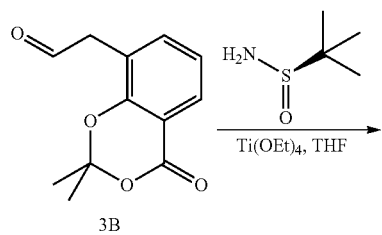
3B

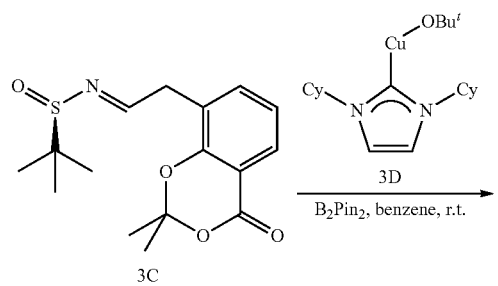
3C

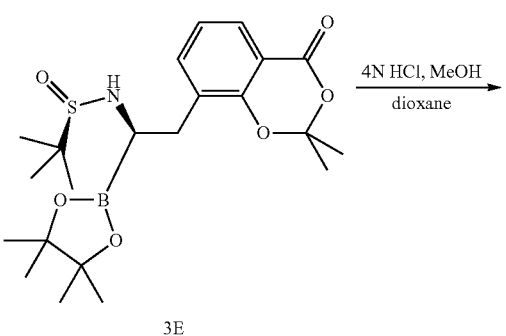
3E

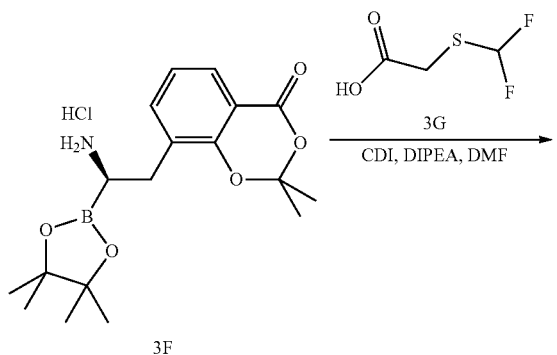
3F

-continued

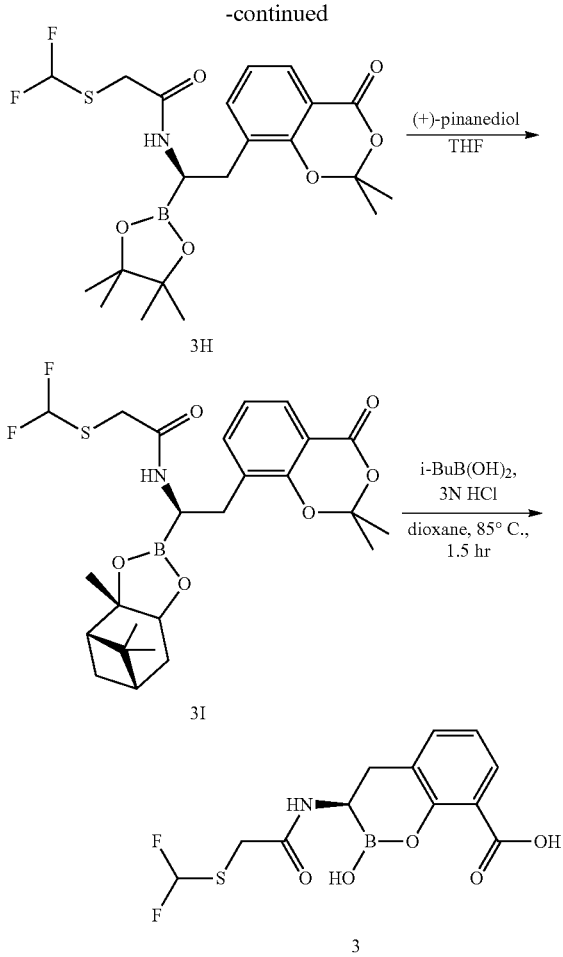

1C was prepared as described in example 1.

Step 1: Synthesis of Compound 3A

The mixture of compound 1C (10.8 g, 33.1 mmol), potassium vinyl trifluoroborate (5.3 g, 39.8 mmol), triethylamine (6.7 g, 9.3 mL, 66.2 mmol) and PdCl$_2$(dppf) (1.35 g, 1.65 mmol) in i-PrOH (200 mL) was degassed for three times and flushed with nitrogen. The mixture was stirred at 85° C. for 1 hour. After concentrated to dryness, the residue was purified by column chromatography (ethyl acetate/hexanes, v/v, 1/100~1/40) to give the titled compound 3A (6.6 g, 98% yield) as a slightly yellow oil.

Step 2: Synthesis of Compound 3B

Benzoquinone (3.85 g, 35.6 mmol) and PdCl$_2$(CH$_3$CN)$_2$ (201 mg, 0.78 mmol) were added into t-BuOH (150 mL) at 85° C., followed by water (0.56 mL, 31 mmol) and compound 3A (6.3 g, 31 mmol). The resulting solution was stirred at 85° C. for 30 minutes until TLC indicating the disappearance of compound 3A. After concentrated to dryness, the residue was purified by column chromatography (ethyl acetate/hexanes, v/v, 1/5~1/2) to give the titled compound 3B (4.1 g, 60% yield) as slightly yellow solid.

Step 3: Synthesis of Compound 3C

To a solution of compound 3B (2.0 g, 9.1 mmol) and (R)-tert-butylsulfinic amide (1.32 g, 10.9 mmol) in THF (40 mL) was added titanium(IV) ethoxide (3.8 mL, 18 mmol). The resulting solution was stirred at room temperature for 20 hours before it was quenched with brine. The mixture was filtered through Celite and washed with EtOAc. The filtrate was concentrated and chromatographed (ethyl acetate/hexanes, v/v, 1/2~1/1) to afford the titled compound 3C (2.04 g, 70% yield) as slightly yellow solid.

Step 4: Synthesis of Compound 3E

The solution of compound 3C (1.9 g, 5.9 mmol), bis(pinacolato)diboron (1.7 g, 6.5 mmol) and NHC-Cu complex 3D (220 mg, 0.60 mmol) (For the synthesis of compound 3D, see: J. Am. Chem. Soc. 2006, 128, 11036) in anhydrous benzene (20 mL) was stirred at room temperature under nitrogen atmosphere for 3 days. The reaction solution was diluted with EtOAc and washed with saturated aqueous NaHCO$_3$ and brine, dried over Na$_2$SO$_4$. After concentration, the residue was quickly chromatographed (20% EtOAc-dichloromethane, silica gel was de-activated with 35 wt % water) to afford the titled compound 3E (2.6 g, quantitative yield) as yellow solid.

Step 5: Synthesis of Compound 3F

To the solution of compound 3E (2.6 g, 5.9 mmol) in dioxane (30 mL) was added methanol (2.4 mL, 59 mmol) and HCl (1.6 mL, 6.5 mmol, 4M in dioxane). The reaction mixture was concentrated to dryness in vacuo and washed with ether/hexanes (v/v, 1/2). The residue (about 2.5 g) was used for next step without further purification.

Step 6: Synthesis of Compound 3H

Difluoromethylsulfanyl-acetic acid 3G (850 mg, 6.0 mmol) and CDI (1.01 g, 6.3 mmol) were dissolved in DMF (15 mL) at stirred at 50° C. for 1 h. After cooling down, compound 3F in 12 mL DMF was added and the solution was stirred at room temperature for 4 hours. The mixture was diluted with hexanes/EtOAc (1/4, v/v) and washed with water (2×) and brine, dried over Na$_2$SO$_4$. After concentration, the crude compound 3H (1.8 g) was obtained as brown greasy solid, which was used directly for the next step.

Step 7: Synthesis of Compound 3I

The crude compound 3H (1.8 g, 3.8 mmol) and (+)-pinanediol (976 mg, 5.7 mmol) were stirred in THF (20 mL) at room temperature for 16 hours before it was concentrated to dryness. The residue was chromatographed (ethyl acetate/hexanes, v/v, 1/2~1/1) to afford the titled compound 3I (1.02 g) as orange oil.

MS calcd for (C$_{25}$H$_{32}$BF$_2$NO$_6$S): 523

MS (ESI, negative) found: (M−1): 522

Step 8: Synthesis of (R)-3-(2-(difluoromethylthio) acetamido)-2-hydroxy-3,4-dihydro-2H-benzo[e][1,2] oxaborinine-8-carboxylic acid (3)

To the solution of compound 3I (1.02 g, 1.95 mmol) in dioxane (50 mL) was added isobutyl boronic acid (800 mg, 7.8 mmol) and 3N aqueous HCl (20 mL). The resulting solution was stirred at 85° C. for 1.5 hours. The mixture was concentrated to about 20 mL and washed with hexanes and then ether. The organic layers were extracted with MeCN/ water (v/v, 1/2). The combined water layer was purified by reverse-phase prep-HPLC to afford 3, (283 mg) as a white solid after lyophilization.

$^1$H NMR (300 MHz, DMSO-d6) δ 10.58 (s, 1H), 10.39 (s, 1H), 7.64 (d, 1H), 7.34 (d, 1H), 7.01 (t, 1H), 6.80-6.96 (m, 1H), 3.60-3.82 (m, 2H), 2.72-3.05 (m, 3H).

MS calcd for ($C_{12}H_{12}BF_2NO_5S$): 331
MS (ESI, positive) found: (M+1): 332
MS (ESI, negative) found: (M−1): 330

Example 4

(R)-3-formamido-2-hydroxy-3,4-dihydro-2H-benzo[e][1,2]oxaborinine-8-carboxylic acid (4)

Scheme 7:

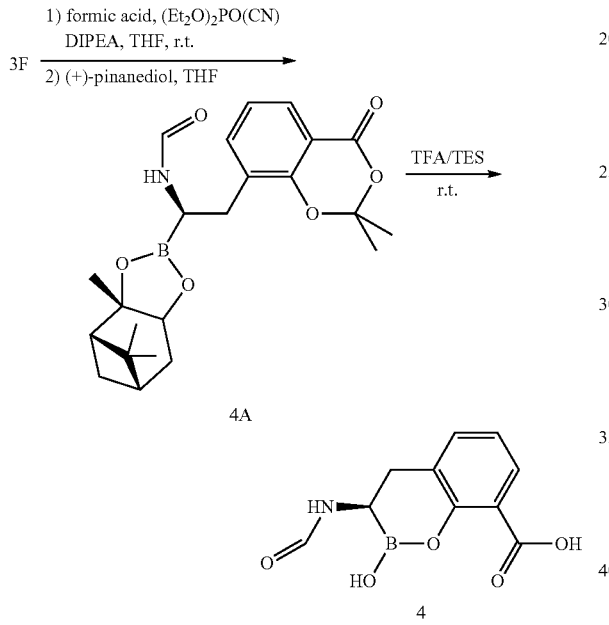

3F was prepared as described in example 3.

Step 1: Synthesis of Compound 4A

To the solution of compound 3F (150 mg, 0.39 mmol) and formic acid (15 mg, 0.32 mmol) in DCM/DMF (3 mL/1 mL) was added TEA (58 mg, 0.58 mmol) and diethyl cyanophosphonate (52 mg, 0.32 mmol). The resulting solution was stirred for 15 hours at room temperature before it was concentrated to dryness in vacuo. The residue was dissolved in THF and (+)-pinanediol (66 mg, 0.39 mmol) was added. After stirring at room temperature for 3 hours, the reaction mixture was concentrated and chromatographed (ethyl acetate/hexanes, v/v, 1/2~1/1) to afford the titled compound 4A (95 mg) as a yellow oil.

MS calcd for ($C_{23}H_{30}BNO_6$): 427
MS (ESI, negative) found: (M−1): 426

Step 2: Synthesis of (R)-3-formamido-2-hydroxy-3,4-dihydro-2H-benzo[e][1,2]oxaborinine-8-carboxylic acid (4)

To the mixture of TFA (6 mL) and triethylsilane (1 mL) was added compound 4A (95 mg, 0.22 mmol). The resulting solution was stirred at 50° C. for 1 hour before it was concentrated to dryness. The residue was washed with $Et_2O$ (20 mL), and purified by prep-HPLC to afford 4, 13.4 mg) as a white solid.

$^1$H NMR (400 MHz, $CD_3OD$) δ 8.09 (s, 1H), 7.83 (d, 1H, J=8.0 Hz), 7.32 (d, 1H, J=6.8 Hz), 6.97 (dd, 1H, J=7.2, 7.2 Hz), 3.22 (s, 1H), 2.97 (s, 2H).

MS calcd for ($C_{10}H_{10}BNO_5$): 235
MS (ESI, positive) found: (M+1): 236
MS (ESI, negative) found: (M−1): 234

Example 5

(R)-3-(2-(5-amino-1,3,4-thiadiazol-2-ylthio)acetamido)-2-hydroxy-3,4-dihydro-2H-benzo[e][1,2]oxaborinine-8-carboxylic acid (5)

Scheme 8:

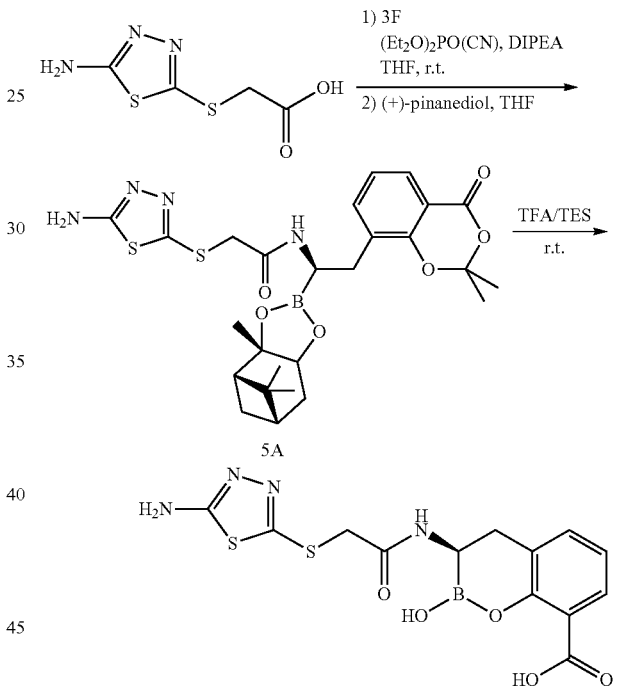

3F was prepared as described in example 3.

Step 1: Synthesis of Compound 5A

To the solution of compound 3F (140 mg, 0.36 mmol) and (5-Amino-[1,3,4]thiadiazol-2-ylsulfanyl)-acetic acid (84 mg, 0.44 mmol) in DCM/DMF (3 mL/1 mL) was added TEA (81 mg, 0.80 mmol) and diethyl cyanophosphonate (71 mg, 0.44 mmol). The resulting solution was stirred for 3 hours at room temperature before it was concentrated to dryness in vacuo. The residue was dissolved in THF and (+)-pinanediol (93 mg, 0.55 mmol) was added. After stirring at room temperature for 15 hours, the reaction mixture was concentrated and the residue was used directly for next step.

MS calcd for ($C_{26}H_{33}BN_4O_6S_2$): 572
MS (ESI, negative) found: (M−1): 571

Step 2: Synthesis of (R)-3-(2-(5-amino-1,3,4-thiadiazol-2-ylthio)acetamido)-2-hydroxy-3,4-dihydro-2H-benzo[e][1,2]oxaborinine-8-carboxylic acid (5)

To the mixture of TFA (6 mL) and triethylsilane (1 mL) was added crude compound 5A. The resulting solution was stirred at 50° C. for 1 hour before it was concentrated to dryness. The residue was washed with $Et_2O$ (20 mL), and purified by prep-HPLC to afford 5 (35 mg) as white solid.

$^1$H NMR (400 MHz, $CD_3OD$) δ 7.79 (dd, 1H, J=1.6, 8.0 Hz), 7.25 (d, 1H, J=7.2 Hz), 6.94 (dd, 1H, J=8.0, 8.0 Hz), 3.90-4.06 (m, 2H), 3.31 (s, 1H), 2.93 (s, 2H).

MS calcd for ($C_{13}H_{13}BN_4O_5S_2$): 380
MS (ESI, positive) found: (M+1): 381
MS (ESI, negative) found: (M−1): 379

Example 6

(R)-2-hydroxy-3-ureido-3,4-dihydro-2H-benzo[e][1,2]oxaborinine-8-carboxylic acid (6)

Scheme 9:

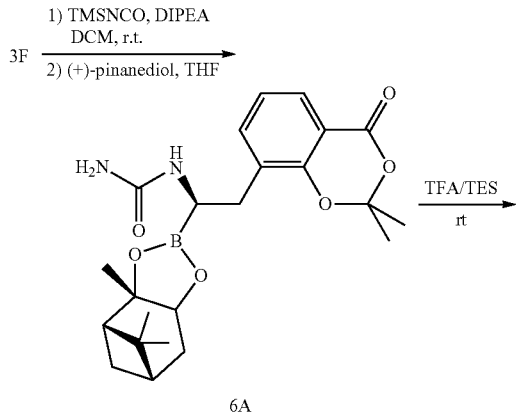

3F was prepared as described in example 3.

Step 1: Synthesis of Compound 6A

To the solution of compound 3F (120 mg, 0.32 mmol) in DCM (3 mL) was added TMSNCO (43 mg, 0.38 mmol) and DIPEA (48 mg, 0.38 mmol). The resulting solution was stirred for 2 hours at room temperature before it was concentrated to dryness in vacuo. The residue was dissolved in THF and (+)-pinanediol (80 mg, 0.47 mmol) was added. After stirring at room temperature for 15 hours, the reaction mixture was concentrated and the residue was used directly for next step.

MS calcd for ($C_{21}H_{31}BN_2O_6$): 442
MS (ESI, negative) found: (M−1): 441

Step 2: Synthesis of (R)-2-hydroxy-3-ureido-3,4-dihydro-2H-benzo[e][1,2]oxaborinine-8-carboxylic acid (6)

To the mixture of TFA (6 mL) and triethylsilane (1.5 mL) was added crude compound 6A. The resulting solution was stirred at 50° C. for 1 hour before it was concentrated to dryness. The residue was washed with $Et_2O$ (20 mL), and purified by prep-HPLC to afford 6 (5.2 mg) as white solid.

$^1$H NMR (400 MHz, $CD_3OD$) δ 7.81 (dd, 1H, J=2.0, 8.0 Hz), 7.30 (d, 1H, J=7.2 Hz), 6.94 (dd, 1H, J=7.6, 7.6 Hz), 3.18 (s, 1H), 2.84 (s, 2H).

MS calcd for ($C_{10}H_{11}BN_2O_5$): 250
MS (ESI, positive) found: (M+1): 251
MS (ESI, negative) found: (M−1): 249

Example 7

(R)-3-(2-(1,3,4-thiadiazol-2-ylthio)acetamido)-2-hydroxy-3,4-dihydro-2H-benzo[e][1,2]oxaborinine-8-carboxylic acid (7)

Scheme 10:

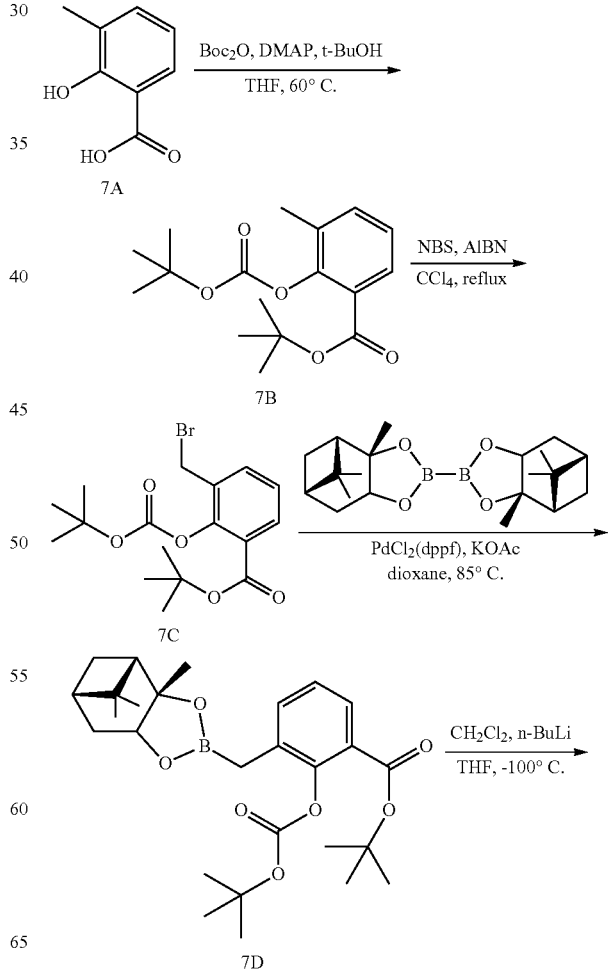

-continued

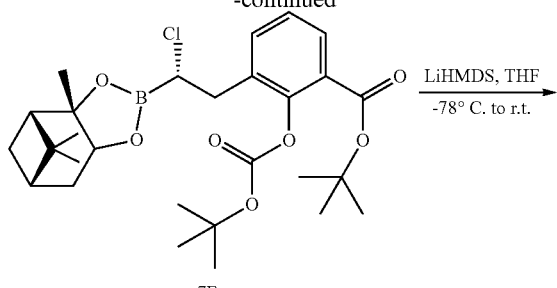

7E

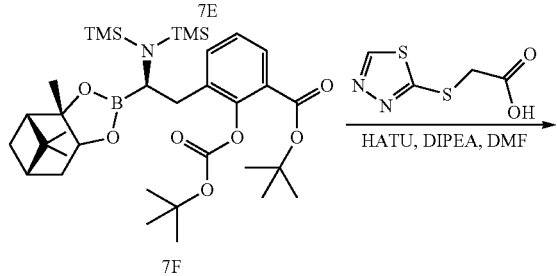

7F

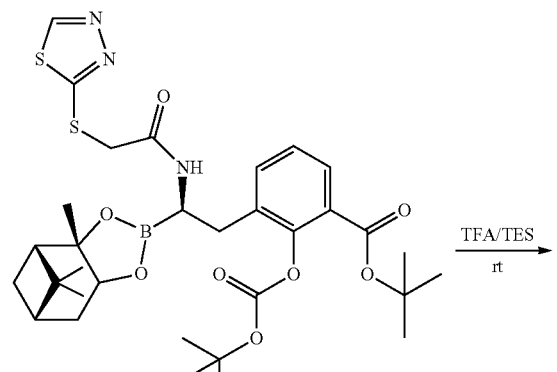

7G

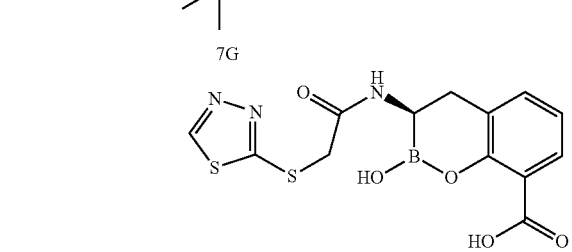

7

Step 1: Synthesis of Compound 7B

To the solution of compound 7A (100 g, 0.657 mol) in THF (400 mL) was added Boc$_2$O (573 g, 2.63 mol), DMAP (24 g, 0.197 mol) and t-BuOH (800 mL). The resulting solution was stirred at 60° C. for 6 hours before it was concentrated in vacuo. The residue was purified by flash column chromatography (ethyl acetate/hexanes, v/v, 1/200~1/100) to give the titled compound 7B (85.9 g, 42.5% yield) as colorless oil.

Step 2: Synthesis of Compound 7C

To the solution of compound 7B (44.3 g, 144 mmol) and NBS (28.1 g, 158 mmol) in CCl$_4$ (400 mL) was added BPO (3.5 g, 14.4 mmol). The resulting mixture was refluxed at 80° C. for 15 hours. The solid was filtered off and the filtrate was concentrated in vacuo. The residue was recrystallized with hexanes to afford the titled compound 7C (32.0 g, 57.6% yield) as white solid.

Step 3: Synthesis of Compound 7D

The mixture of compound 7C (47.5 g, 123 mmol), bis(pinanediolato)diboron (39.9 g, 112 mmol), KOAc (32.9 g, 336 mmol) and PdCl$_2$(dppf) (4.5 g, 5.6 mmol) in dioxane (500 mL) was degassed for three times and flushed with nitrogen. The mixture was stirred at 95° C. for 8 hours. After concentrated to dryness, the residue was purified by column chromatography (ethyl acetate/hexanes, v/v, 1/200~1/100) to give the titled compound 7D (40 g, 59% yield) as slightly yellow oil.

Step 4: Synthesis of Compound 7E

To a solution of CH$_2$Cl$_2$ (4.2 mL, 65.8 mmol) in THF (160 mL) at −100° C. was added 2.5 M n-butyl lithium in hexane (18.4 mL, 46.0 mmol) slowly under nitrogen and down the inside wall of the flask, maintaining the temperature below −90° C. The reaction mixture was stirred at −100° C. for another 30 minutes before the addition of Compound 7D from step 3 (16.0 g, 32.9 mmol) in THF (30 mL) at −90° C. and then the reaction was allowed to warm to room temperature where it was stirred for 16 h. The reaction was concentrated in vacuo directly to dryness and then chromatographed (100% hexane-20% EtOAc-hexane) to obtain the titled compound 7E (15.0 g, 85% yield) as slightly yellow oil.

Step 5: Synthesis of Compound 7F

Compound 7E (14.1 g, 26.4 mmol) in THF (100 mL) was cooled to −78° C. under nitrogen. A solution of LiHMDS (27 mL, 1.0M in THF, 27.0 mmol) was added slowly at −78° C. Upon completion of the addition, the reaction flask was allowed to warm to room temperature. After stirring at room temperature for 2 h, the reaction mixture was concentrated under vacuum and hexane (100 mL) was added. The precipitated lithium salts were filtered off through a Celite pad, rinsed with additional hexane, and the combined filtrates were concentrated under vacuum to give crude bis(trimethylsilyl)amine product 7F (26.4 mmol), which was stored as a stock solution for future use.

MS calcd for (C$_{34}$H$_{58}$BNO$_7$Si$_2$): 659
MS (ESI, positive) found: (M−2*TMS+3): 516

Step 6: Synthesis of Compound 7G

To the solution of ([1,3,4]Thiadiazol-2-ylsulfanyl)-acetic acid (655 mg, 3.72 mmol) in DCM/DMF (10 mL/5 mL) was added HATU (1.40 g, 3.72 mmol) at 0° C. After stirring at 0° C. for 15 minutes, a solution of bis(trimethylsilyl)amine compound 7F (3.4 mmol) in DCM (5 mL) was added, followed by DIPEA (0.71 mL, 4.08 mmol). The resulting mixture was warmed up and stirred at room temperature for 1 hour, extracted with DCM (50 mL*3), washed with water and brine, dried over Na$_2$SO$_4$. The concentrated material was then chromatographed (EtOAc-hexane: v/v: 10/1~1/1) to obtain the titled compound 7G (1.35 g, 59% yield) as a slightly yellow greasy solid.

MS calcd for (C$_{32}$H$_{44}$BN$_3$O$_8$S$_2$): 673
MS (ESI, negative) found: (M+Na): 672

Step 7: Synthesis of (R)-3-(2-(1,3,4-thiadiazol-2-ylthio)acetamido)-2-hydroxy-3,4-dihydro-2H-benzo[e][1,2]oxaborinine-8-carboxylic acid (7)

To the mixture of TFA (40 mL) and triethylsilane (6 mL) was added compound 7G (1.35 g, 2.01 mmol). The resulting solution was stirred at room temperature for 1 hour before it was concentrated to dryness. The residue was washed with $Et_2O$ (3×20 mL), and dissolved in $CH_3CN/H_2O$ (20 mL/20 mL), dried by lyophilization to afford 7 (380 mg, 52% yield) as a white solid.

$^1$H NMR (400 MHz, $CD_3OD$) δ 9.28 (s, 1H), 7.73 (d, 1H, J=7.6 Hz), 7.15 (d, 1H, J=7.2 Hz), 6.84 (dd, 1H, J=7.6, 7.6 Hz), 4.13-4.29 (m, 2H), 3.30 (s, 1H), 2.91 (d, 2H, J=3.2 Hz).

MS calcd for ($C_{13}H_{12}BN_3O_5S_2$): 365
MS (ESI, positive) found: (M+1): 366
MS (ESI, negative) found: (M−1): 364

Example 8

(R)-3-(2-azidoacetamido)-2-hydroxy-3,4-dihydro-2H-benzo[e][1,2]oxaborinine-8-carboxylic acid (8)

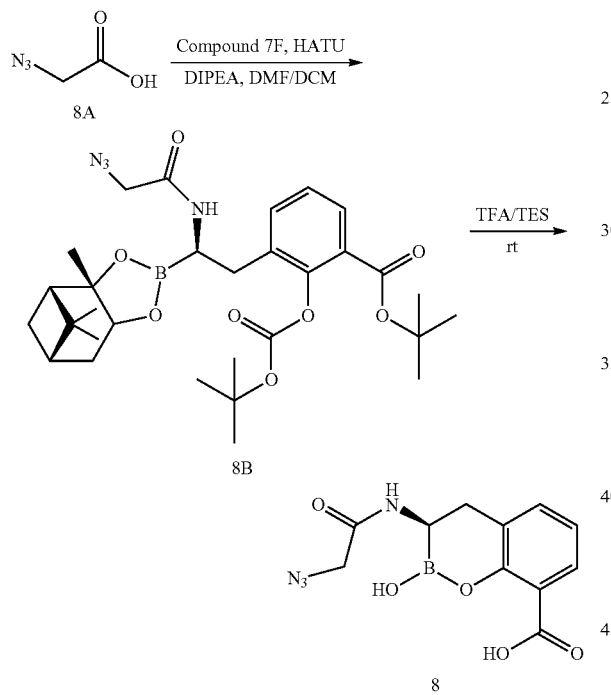

7F was prepared as described in example 7.

Step 1: Synthesis of Compound 8B

To the solution of 2-azidoacetic acid (8A) (*J. Med. Chem.*, 2011, 54, 7375) (544 mg, 5.4 mmol) in DCM/DMF (20 mL/10 mL) was added HATU (2.05 g, 5.4 mmol) at 0° C. After stirring at 0° C. for 15 minutes, a solution of bis(trimethylsilyl)amine compound F (3.59 mmol) in DCM (10 mL) was added, followed by DIPEA (0.94 mL, 5.4 mmol). The resulting mixture was warmed up and stirred at room temperature overnight, extracted with DCM (50 mL*3), washed with water and brine, dried over $Na_2SO_4$. The concentrated material was then chromatographed (EtOAc-hexane: v/v: 10/1~1/1) to obtain the titled compound 8B (582 mg, 27% yield) as a slightly yellow greasy solid.

MS calcd for ($C_{30}H_{43}BN_4O_8$): 598
MS (ESI, negative) found: (M−1): 597

Step 2: Synthesis of (R)-3-(2-azidoacetamido)-2-hydroxy-3,4-dihydro-2H-benzo[e][1,2]oxaborinine-8-carboxylic acid (8)

To the mixture of TFA (46 mL) and triethylsilane (8 mL) was added compound 8B (582 mg, 0.97 mmol). The resulting solution was stirred at room temperature for 1 hour before it was concentrated to dryness. The residue was partitioned in 20 mL water and 20 mL ether. The aqueous layer was washed with ether (2×20 mL) and dried by lyophilization to afford (8, 120 mg, 43% yield) as white solid.

$^1$H NMR (400 MHz, $CD_3OD$) δ 7.83 (dd, 1H, J=2.0, 8.4 Hz), 7.31 (d, 1H, J=5.4 Hz), 6.97 (dd, 1H, J=7.6, 7.6 Hz), 4.25 (d, 2H, J=5.2 Hz), 3.31 (s, 1H), 2.97 (d, 2H, J=3.2 Hz).

MS calcd for ($C_{11}H_{11}BN_4O_5$): 290
MS (ESI, positive) found: (M+1): 291
MS (ESI, negative) found: (M−1): 289

Example 9

(R)-3-(2-(dimethylamino)-2-oxoacetamido)-2-hydroxy-3,4-dihydro-2H-benzo[e][1,2]oxaborinine-8-carboxylic acid (9)

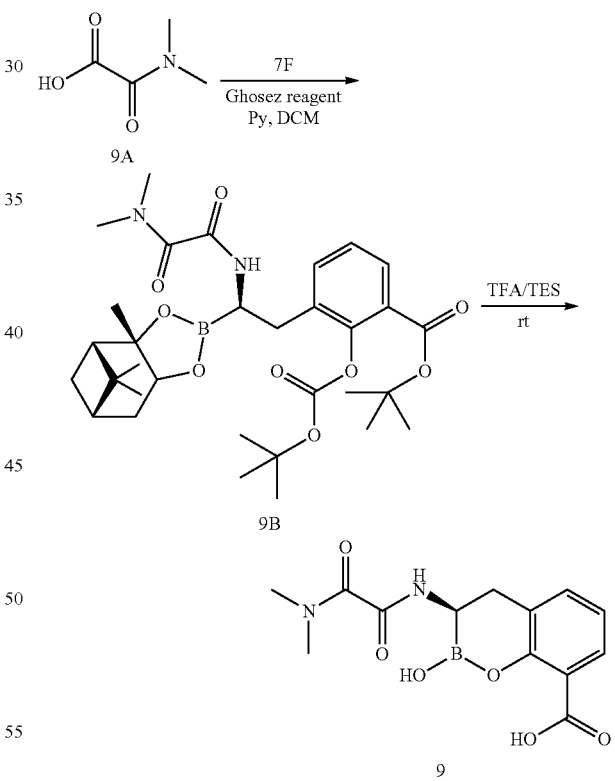

7F was prepared as described in example 7.

Step 1: Synthesis of 9B

To the solution of N,N-Dimethyl-oxalamic acid 9A (*Heterocycles*, 1993, 36, 2687) (125 mg, 1.07 mmol) in DCM (3 mL) was added Ghosez reagent (157 mg, 1.18 mmol) at 0° C. After stirring at 0° C. for 30 minutes, a solution of compound 7F in pyridine (1 mL) was added into the reaction mixture.

The resulting mixture was stirred at room temperature for 3 hours before it was concentrated to dryness. The residue was dissolved in EtOAc, washed with water and brine, dried over Na$_2$SO$_4$. After concentration, the crude 9B (157 mg) was obtained as yellow oil, which was used for next step without further purification.

MS calcd for (C$_{32}$H$_{47}$BN$_2$O$_9$): 614
MS (ESI, negative) found: (M−1): 613

Step 2: Synthesis of (R)-3-(2-(dimethylamino)-2-oxoacetamido)-2-hydroxy-3,4-dihydro-2H-benzo[e][1,2]oxaborinine-8-carboxylic acid (9)

To the mixture of 90% TFA (2 mL) and triethylsilane (0.5 mL) was added compound 9B (157 mg, crude). The resulting solution was stirred at room temperature for 1 hour before it was concentrated to dryness. The residue purified by reverse-phase prep-HPLC to afford 9, (5.4 mg) as white solid.

$^1$H NMR (400 MHz, CD$_3$OD) δ 7.82 (d, 1H, J=7.6 Hz), 7.34 (d, 1H, J=6.8 Hz), 6.98 (dd, 1H, J=7.6, 7.6 Hz), 3.37 (s, 1H), 2.85-3.05 (m, 2H), 2.88 (s, 3H), 2.55 (s, 3H).
MS calcd for (C$_{13}$H$_{15}$BN$_2$O$_6$): 306
MS (ESI, positive) found: (M+1): 307
MS (ESI, negative) found: (M−1): 305

Example 10

(R)-3-(3-(dimethylamino)-3-oxopropanamido)-2-hydroxy-3,4-dihydro-2H-benzo[e][1,2]oxaborinine-8-carboxylic acid (10)

Scheme 13:

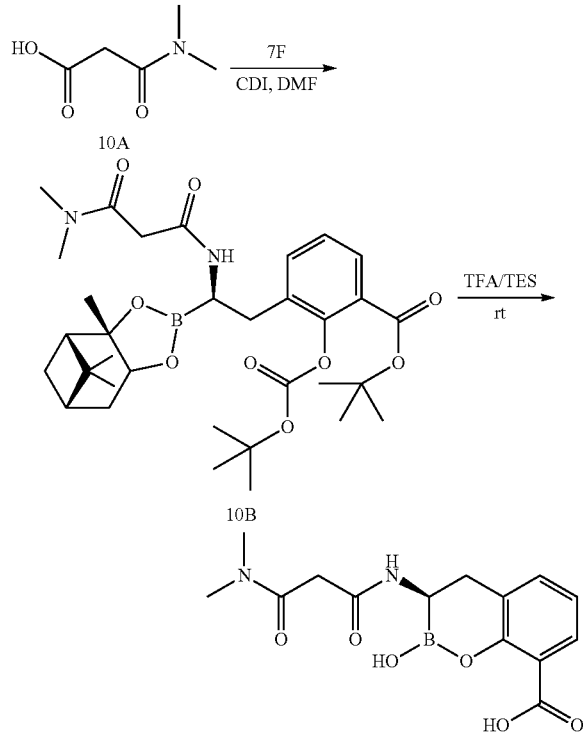

7F was prepared as described in example 7.

Step 1: Synthesis of 10B

Bis(trimethylsilyl)amine compound 7F (300 mg, 0.5 mmol) was stirred in MeOH/THF (1 mL/5 mL) for 30 min at room temperature before it was concentrated to dryness in vacuo to afford the free amine as a yellow oil. Compound 10A (WO 09117540) (76 mg, 0.58 mmol) and CDI (94 mg, 0.58 mmol) were dissolved in DMF (2 mL) at stirred at 45° C. for 1 h. After cooling down, the free amine obtained above in 1 mL DMF was added and was stirred at room temperature for 15 hours. The mixture was diluted with DCM and washed with water and brine, dried over Na$_2$SO$_4$. After concentration, the crude titled compound 10B (345 mg) was obtained as slightly yellow oil, which was used for next step without further purification.

MS calcd for (C$_{33}$H$_{49}$BN$_2$O$_9$): 628
MS (ESI, negative) found: (M−1): 627

Step 2: Synthesis of (R)-3-(3-(dimethylamino)-3-oxopropanamido)-2-hydroxy-3,4-dihydro-2H-benzo[e][1,2]oxaborinine-8-carboxylic acid (10)

To the mixture of 90% TFA (7 mL) and triethylsilane (2 mL) was added compound 10B (325 mg, crude). The resulting solution was stirred at room temperature for 1 hour before it was concentrated to dryness. The residue purified by reverse-phase prep-HPLC to afford 10 (40 mg) as white solid.

$^1$H NMR (400 MHz, CD$_3$OD) δ 7.83 (d, 1H, J=6.4 Hz), 7.32 (d, 1H, J=7.6 Hz), 6.96 (dd, 1H, J=7.6, 7.6 Hz), 3.54-3.56 (m, 2H), 3.31 (s, 1H), 2.96 (d, 2H, J=3.2 Hz), 2.82 (d, 6H, J=2.0 Hz).
MS calcd for (C$_{14}$H$_{17}$BN$_2$O$_6$): 320
MS (ESI, positive) found: (M+1): 321
MS (ESI, negative) found: (M−1): 319

Example 11

(R)-2-hydroxy-3-(methylthiocarbonylamino)-3,4-dihydro-2H-benzo[e][1,2]oxaborinine-8-carboxylic acid (11)

Scheme 14:

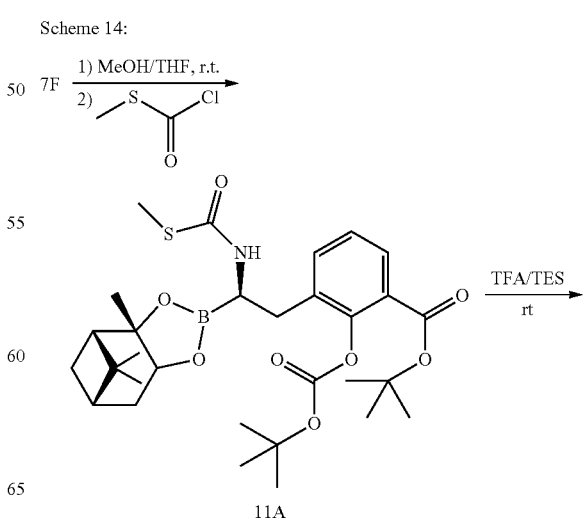

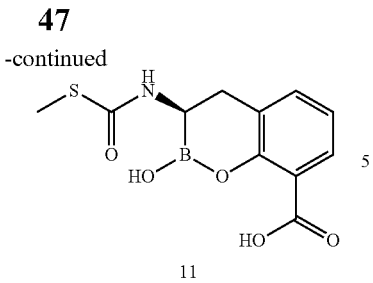

11

7F was prepared as described in example 7.

Step 1: Synthesis of 11A

Bis(trimethylsilyl)amine compound 7F (0.4 mmol) was stirred in MeOH/THF (0.5 mL/2 mL) for 30 min at room temperature before it was concentrated to dryness in vacuo to afford the free amine as a yellow oil. The free amine was dissolved in DCM (2 mL) and pyridine (38 mg, 0.48 mmol) was added, followed by methyl chlorothiolformate (53 mg, 0.4 mmol). After stirring at room temperature for 12 hours, the reaction mixture was diluted with DCM, washed with water and brine, dried over $Na_2SO_4$. After concentration, the crude titled compound 11A (280 mg) was obtained as yellow oil, which was used for next step without further purification.

MS calcd for ($C_{30}H_{44}BNO_8S$): 589
MS (ESI, negative) found: (M−1): 588

Step 2: Synthesis of (R)-2-hydroxy-3-(methylthio-carbonylamino)-3,4-dihydro-2H-benzo[e][1,2]ox-aborinine-8-carboxylic acid (11)

To the mixture of TFA (2 mL) and triethylsilane (0.5 mL) was added compound C1 (280 mg, crude). The resulting solution was stirred at room temperature for 1 hour before it was concentrated to dryness. The residue purified by reverse-phase prep-HPLC to afford 11 (30 mg) as white solid.

$^1$H NMR (400 MHz, $CD_3OD$) δ 7.85 (dd, 1H, J=1.2, 8.0 Hz), 7.31 (d, 1H, J=7.6 Hz), 6.97 (dd, 1H, J=7.2, 8.0 Hz), 3.30 (s, 1H), 2.91 (s, 2H), 2.39 (s, 3H).

MS calcd for ($C_{11}H_{12}BNO_5S$): 281
MS (ESI, positive) found: (M+1): 282
MS (ESI, negative) found: (M−1): 280

Example 12

(R)-2-hydroxy-3-(nicotinamido)-3,4-dihydro-2H-benzo[e][1,2]oxaborinine-8-carboxylic acid (12)

Scheme 15:

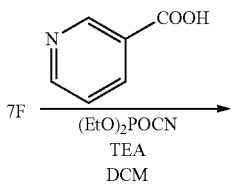

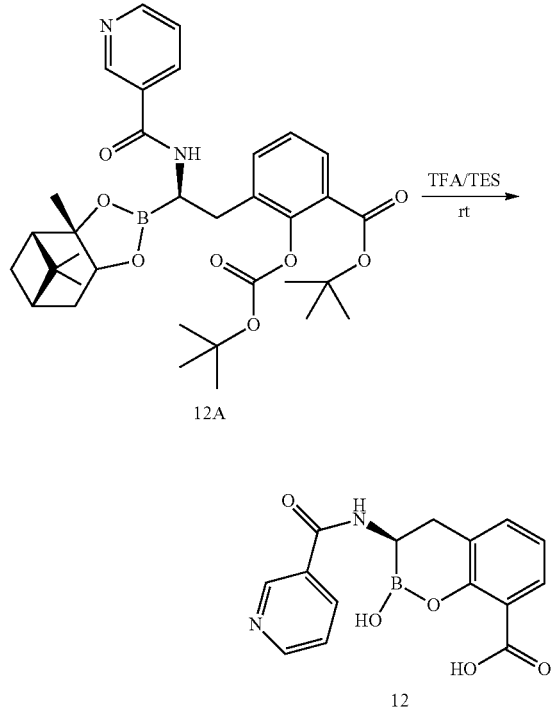

12

Intermediate 7F was made as described in example 7.

Step 1: Synthesis of 12A

To the solution of compound 7F (4 mmol, crude) and 3-pyridinecarboxylic acid (492 mg, 4 mmol) in DMF (40 mL) was added $(EtO)_2POCN$ (652 mg, 4 mmol). The resulting reaction mixture was stirred at room temperature overnight before it was concentrated. The residue was dissolved in DCM and washed with water, brine and dried over $Na_2SO_4$. Column chromatography gave titled compound 12A (1.311 g) as slightly yellow oil.

MS calcd for ($C_{34}H_{45}BN_2O_8$): 620
MS (ESI, negative) found: (M−1): 619

Step 2: Synthesis of (R)-2-hydroxy-3-(nicotina-mido)-3,4-dihydro-2H-benzo[e][1,2]oxaborinine-8-carboxylic acid (12)

To the mixture of TFA (56 mL) and triethylsilane (16 mL) was added compound 12A (1.311 g). The resulting solution was stirred at room temperature for 1 hour before it was concentrated to dryness. The residue was washed with ether to afford 12 (450 mg) as white solid.

$^1$H NMR (400 MHz, $CD_3OD$) δ 9.18 (m, 1H), 8.98 (m, 1H), 8.42 (m, 1H), 7.98 (m, 1H), 7.76 (m, 1H,), 7.52 (m, 1H), 7.12 (m, 1H), 3.69 (s, 1H), 3.26 (s, 2H).

MS calcd for ($C_{15}H_{13}BN_2O_5$): 312
MS (ESI, positive) found: (M+1): 313
MS (ESI, negative) found: (M−1): 311

Example 13

(R)-2-hydroxy-3-(2-(methylthio)acetamido)-3,4-dihydro-2H-benzo[e][1,2]oxaborinine-8-carboxylic acid (13)

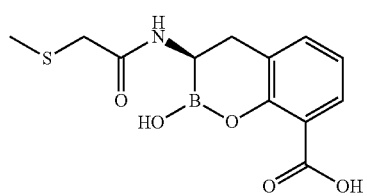

(R)-2-hydroxy-3-(2-(methylthio)acetamido)-3,4-dihydro-2H-benzo[e][1,2]oxaborinine-8-carboxylic acid (13) was prepared following similar sequence described in example 7 (steps 1-7) replacing ([1,3,4]Thiadiazol-2-ylsulfanyl)-acetic acid in step 6 with 2-(methylthio)acetic acid.

$^1$H NMR (400 MHz, CD$_3$OD) δ 7.84 (d, 1H, J=8.0 Hz), 7.33 (d, 1H, J=7.2 Hz), 6.98 (d, 1H, J=7.6 Hz), 3.33 (S, 1H), 3.20 (s, 2H), 2.97 (s, 2H), 1.70 (s, 3H).

MS calcd for (C$_{12}$H$_{14}$BNO$_5$S): 295
MS (ESI, positive) found: (M+1): 296
MS (ESI, negative) found: (M−1): 294

Example 14

(R)-3-(5-fluoronicotinamido)-2-hydroxy-3,4-dihydro-2H-benzo[e][1,2]oxaborinine-8-carboxylic acid (14)

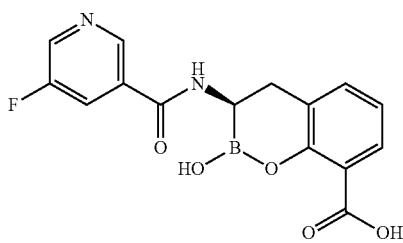

(R)-3-(5-fluoronicotinamido)-2-hydroxy-3,4-dihydro-2H-benzo[e][1,2]oxaborinine-8-carboxylic acid (14) was prepared following similar sequence described in example 7 (steps 1-7) replacing ([1,3,4]Thiadiazol-2-ylsulfanyl)-acetic acid in step 6 with 5-fluoronicotinic acid.

$^1$H NMR (400 MHz, CD$_3$OD) δ 11.10 (s, 1H), 8.84 (d, 2H, J=15.6 Hz), 8.10 (d, 1H, J=8.8 Hz), 7.63 (d, 1H, J=7.2 Hz), 7.29 (d, 1H, J=6.8 Hz), 6.87 (t, 1H, J=7.6 Hz), 3.25 (s, 1H), 2.95 (s, 2H).

MS calcd for (C$_{15}$H$_{12}$BFN$_2$O$_5$): 330
MS (ESI, positive) found: (M+1): 331
MS (ESI, negative) found: (M−1): 329

Example 15

(R)-2-hydroxy-3-(thiazole-5-carboxamido)-3,4-dihydro-2H-benzo[e][1,2]oxaborinine-8-carboxylic acid (15)

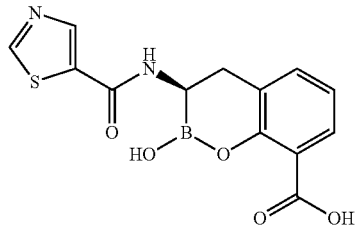

(R)-2-hydroxy-3-(thiazole-5-carboxamido)-3,4-dihydro-2H-benzo[e][1,2]oxaborinine-8-carboxylic acid (15) was prepared following similar sequence described in example 7 (steps 1-7) replacing ([1,3,4]Thiadiazol-2-ylsulfanyl)-acetic acid in step 6 with thiazole-5-carboxylic acid.

$^1$H NMR (400 MHz, CD$_3$OD) δ 9.31 (s, 1H), 8.57 (s, 1H), 7.81 (d, 1H, J=8.0 Hz), 7.33 (d, 1H, J=7.6 Hz), 6.94 (t, 1H, J=8.0 Hz), 3.48 (s, 1H), 3.05 (s, 2H).

MS calcd for (C$_{15}$H$_{12}$BFN$_2$O$_5$): 318
MS (ESI, positive) found: (M+1): 319
MS (ESI, negative) found: (M−1): 317

Example 16

(R)-3-(3-amino-3-oxopropanamido)-2-hydroxy-3,4-dihydro-2H-benzo[e][1,2]oxaborinine-8-carboxylic acid (16)

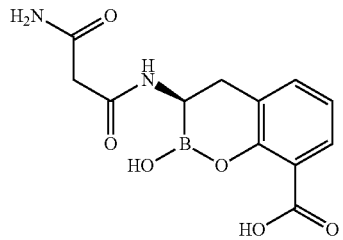

(R)-3-(3-amino-3-oxopropanamido)-2-hydroxy-3,4-dihydro-2H-benzo[e][1,2]oxaborinine-8-carboxylic acid (16) was prepared following similar sequence described in example 8 replacing 2-azidoacetic acid in step 1 with 3-amino-3-oxopropanoic acid.

$^1$H NMR (400 MHz, CD$_3$OD) δ 7.82 (dd, 1H, J=1.2, 8.0 Hz), 7.31 (d, 1H, J=6.4 Hz), 6.94 (dd, 1H, J=7.2, 7.2 Hz), 3.27-3.32 (m, 3H), 2.95 (d, 2H, J=3.6 Hz).

MS calcd for (C$_{12}$H$_{13}$BN$_2$O$_6$): 292
MS (ESI, positive) found: (M+1): 293
MS (ESI, negative) found: (M−1): 291

Example 17

(R)-3-(2-amino-2-oxoacetamido)-2-hydroxy-3,4-dihydro-2H-benzo[e][1,2]oxaborinine-8-carboxylic acid (17)

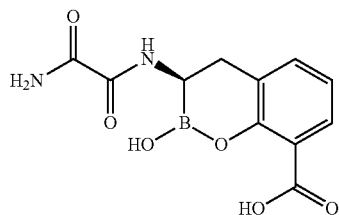

(R)-3-(2-amino-2-oxoacetamido)-2-hydroxy-3,4-dihydro-2H-benzo[e][1,2]oxaborinine-8-carboxylic acid (17) was prepared following similar sequence described in example 8 replacing 2-azidoacetic acid in step 1 with 2-amino-2-oxoacetic acid.

$^1$H NMR (400 MHz, CD$_3$OD) δ 7.82 (d, 1H, J=8.0 Hz), 7.31 (d, 1H, J=7.2 Hz), 6.96 (dd, 1H, J=7.6, 7.6 Hz), 3.39 (t, 1H, J=4.0 Hz), 2.98 (d, 2H, J=3.6 Hz).

MS calcd for (C$_{11}$H$_{11}$BN$_2$O$_6$): 278
MS (ESI, positive) found: (M-H2O+1): 261
MS (ESI, negative) found: (M-1): 277

Example 18

(R)-2-hydroxy-3-(pyrimidine-5-carboxamido)-3,4-dihydro-2H-benzo[e][1,2]oxaborinine-8-carboxylic acid (18)

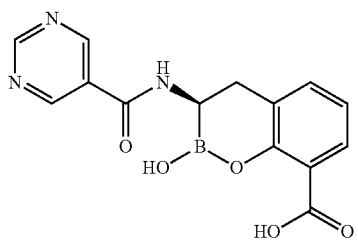

(R)-2-hydroxy-3-(pyrimidine-5-carboxamido)-3,4-dihydro-2H-benzo[e][1,2]oxaborinine-8-carboxylic acid (18) was prepared following similar sequence described in example 8 replacing 2-azidoacetic acid in step 1 with pyrimidine-5-carboxylic acid.

$^1$H NMR (400 MHz, CD$_3$OD) δ 9.34 (s, 1H), 9.16 (s, 2H), 7.80 (d, 1H, J=6.8 Hz), 7.34 (d, 1H, J=6.4 Hz), 6.94 (dd, 1H, J=7.6, 7.6 Hz), 3.51 (t, 1H, J=3.6 Hz), 3.09 (s, 2H).

MS calcd for (C$_{14}$H$_{12}$BN$_3$O$_5$): 313
MS (ESI, positive) found: (M+1): 314
MS (ESI, negative) found: (M-1): 312

Example 19

(R)-3-(5-amino-1,3,4-thiadiazole-2-carboxamido)-2-hydroxy-3,4-dihydro-2H-benzo[e][1,2]oxaborinine-8-carboxylic acid (19)

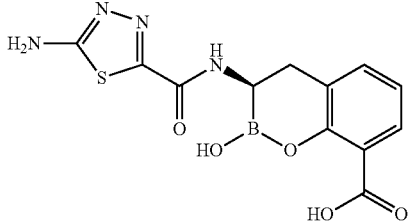

(R)-3-(5-amino-1,3,4-thiadiazole-2-carboxamido)-2-hydroxy-3,4-dihydro-2H-benzo[e][1,2]oxaborinine-8-carboxylic acid (19) was prepared following similar sequence described in example 7 (steps 1-7) replacing ([1,3,4]Thiadiazol-2-ylsulfanyl)-acetic acid in step 6 with 5-(tert-butoxycarbonylamino)-1,3,4-thiadiazole-2-carboxylic acid (WO2010/144338).

$^1$H NMR (400 MHz, CD$_3$OD) δ 7.78 (dd, 1H, J=0.8, 8.0 Hz), 7.32 (d, 1H, J=6.8 Hz), 6.95 (dd, 1H, J=8.0, 8.0 Hz), 3.43 (t, 1H, J=3.6 Hz), 3.01-3.04 (m, 2H).

MS calcd for (C$_{12}$H$_{11}$BN$_4$O$_5$S): 334
MS (ESI, positive) found: (M+1): 335
MS (ESI, negative) found: (M-1): 333

Example 17

Potentiation of Aztreonam

The potency and spectrum of β-lactamase inhibitors (BLIs) was determined by assessing their aztreonam potentiation activity in a dose titration potentiation assay using strains of various bacteria that are resistant to aztreonam due to expression of various β-lactamases. Aztreonam is a monobactam antibiotic and is hydrolyzed by the majority of beta-lactamases that belong to class A or C (but not class B or D). The potentiation effect was observed as the ability of BLI compounds to inhibit growth in the presence of sub-inhibitory concentration of aztreonam. MICs of test strains varied from 64 µg/mL to >128 µg/mL. Aztreonam was present in the test medium at 4 µg/mL. Compounds were tested at concentrations up to 40 µg/mL. In this assay potency of compounds was reported as the minimum concentration of BLI required to inhibit growth of bacteria in the presence of 4 µg/mL of aztreonam (MPC$_{@4}$). Table 1 summarizes the BLI potency of aztreonam potentiation (MPC$_{@4}$) for various strains overexpressing class A (ESBL and KPC), and class C beta-lactamases. Aztreonam MIC for each strain is also shown. The results were compared to comparative compounds A and B:

Compound A

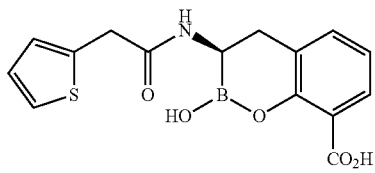

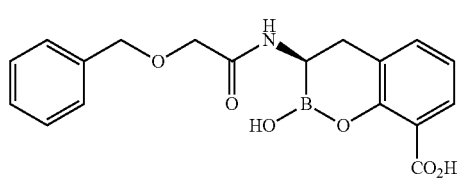
Compound B

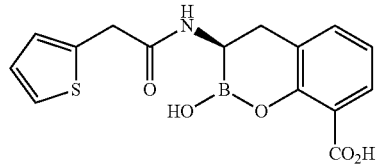
Compound A

TABLE 1

Activity of BLIs to potentiate aztreonam against strains expressing class A and class C enzymes.

| Aztreonam MIC (µg/mL) | >128 | >128 | >128 | 64 | 128 | >128 | 64 | >128 |
|---|---|---|---|---|---|---|---|---|
| | AZT MPC$_4$ CTX-M-14 KP1005 | AZT MPC$_4$ CTX-M-15 KP1009 | AZT MPC$_4$ SHV-5 ec308 | AZT MPC$_4$ SHV-12 KP1010 | AZT MPC$_4$ TEM-10 ec302 | AZT MPC$_4$ K-2 KP1004 | AZT MPC$_4$ ECL1002 | AZT MPC$_4$ CMY-6 EC1010 |
| CPD A | Y | Y | X | X | Y | Y | Y | Y |
| CPD B | Z | Z | Y | Y | Z | Z | Z | Z |
| 2 | X | Y | X | X | Y | Y | Y | Y |
| 1 | Y | Y | X | X | Y | Y | Y | Y |
| 3 | X | Y | X | X | Y | Y | Y | X |
| 4 | Y | Y | Y | X | Y | X | Y | X |
| 8 | X | X | X | X | Y | X | Y | X |
| 5 | X | X | X | X | Y | Y | Y | X |
| 6 | Y | Y | Y | Y | Z | X | Z | Y |
| 7 | X | X | X | X | Y | Y | Y | X |
| 9 | Y | Y | X | X | Y | Y | Y | Y |
| 10 | Y | X | Y | X | Y | X | Y | X |
| 11 | Y | Y | X | X | Y | Y | Y | Y |
| 12 | Y | Y | Y | X | X | Y | X | Y |
| 13 | X | X | X | X | Y | X | X | X |
| 14 | Y | Y | Y | X | Y | Y | Y | Y |
| 15 | Y | Y | X | X | X | Y | Y | Y |
| 16 | X | X | X | X | X | Y | X | X |
| 17 | Y | Y | X | X | X | Y | Y | Y |
| 18 | Y | Y | Y | X | X | Y | Y | Y |
| 19 | Y | Y | X | X | Y | Y | Y | X |

X = MIC of less than 1 µg/mL
Y = MIC of 1 µg/mL to 10 µg/mL
Z = MIC of greater than 10 µg/mL

Example 18

Potentiation of Tigemonam

Selected β-lactamase inhibitors were also tested for their ability to potentiate the monobactam tigemonam. The potentiation effect is observed as the ability of BLI compounds to inhibit growth in the presence of sub-inhibitory concentration of tigemonam. MICS of test strains varied from 16 µg/mL to >64 µg/mL. Tigemonam was present in the test medium at 4 µg/mL. Compounds were tested at concentrations up to 40 µg/mL. In this assay potency of compounds was reported as the minimum concentration of BLI required to inhibit growth of bacteria in the presence of 4 µg/mL of aztreonam (MPC$_{@4}$). Table 2 summarizes the BLI potency of tigemonam potentiation (MPC$_{@4}$) for various strains overexpressing class A (ESBL) and class C beta-lactamases. Tigemonam MIC for each strain is also shown. The results were compared to comparative compounds A and B:

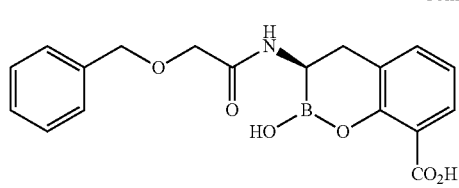
Compound B

TABLE 2

Activity of BLIs to potentiate tigemonam against strains expressing class A and class C enzymes.

| Tigemonam MIC (µg/mL) | >64 | >64 | >64 | >64 | >64 | 32 | 16 |
|---|---|---|---|---|---|---|---|
| | TIG MPC$_4$ CTX- | TIG MPC$_4$ CTX- | TIG MPC$_4$ SHV- | TIG MPC$_4$ | TIG MPC$_4$ TEM- | TIG | TIG MPC$_4$ |

TABLE 2-continued

Activity of BLIs to potentiate tigemonam against strains expressing class A and class C enzymes.

| | M-14 KP1005 | M-15 KP1009 | 5 ec308 | SHV-12 KP1010 | 10 ec302 | MPC$_4$ ECL1002 | CMY-6 EC1010 |
|---|---|---|---|---|---|---|---|
| CPD A | Y | Y | Y | X | Z | Y | X |
| CPD B | Z | Z | Y | Y | Z | Y | Y |
| 2 | X | Y | Y | X | Y | X | X |
| 1 | Y | Y | X | X | Z | X | X |
| 3 | X | X | X | X | Y | Y | X |
| 4 | Y | Y | Y | X | Z | X | X |
| 8 | X | X | Y | X | Y | X | X |
| 5 | X | X | Y | X | Y | X | X |
| 6 | Z | Y | Z | Y | Z | Y | X |
| 7 | X | X | X | X | Y | Y | X |
| 9 | Y | Y | Y | Y | Z | Y | Y |
| 10 | Y | X | Y | X | Z | X | X |
| 11 | Y | Y | Y | X | Z | Y | X |
| 12 | Y | Y | Y | X | Y | X | Y |
| 13 | X | X | X | X | Y | X | X |
| 14 | Y | Y | Y | X | Y | Y | Y |
| 15 | Y | Y | Y | X | Y | Y | Y |
| 16 | Y | X | Y | X | Y | X | X |
| 17 | Z | Y | Y | Y | X | Y | X |
| 18 | Y | Y | Y | X | Y | Y | X |
| 19 | Y | Y | X | X | Y | Y | X |

X = MIC of less than 1 μg/mL
Y = MIC of 1 μg/mL to 10 μg/mL
Z = MIC of greater than 10 μg/mL

Example 19

Potentiation of Biapenem

β-lactamase inhibitors were also tested for their ability to potentiate the carbapenem biapenem against strains producing class A (KPC) and class D (OXA-48) carbapenemases. The potentiation effect is observed as the ability of BLI compounds to inhibit growth in the presence of a sub-inhibitory concentration of biapenem. Biapenem MIC of test strains were 16-32 μg/mL. Biapenem was present in the test medium at 1 μg/mL. Compounds were tested at concentrations up to 40 μg/mL. In this assay potency of compounds was reported as the minimum concentration of BLI required to inhibit growth of bacteria in the presence of 1 μg/mL of biapenem (MPC$_{@1}$). Table 3 summarizes the BLI potency of biapenem potentiation (MPC$_{@1}$) for two strains overexpressing class A (KPC) and class D (OXA-48) carbapenemases. Biapenem MIC for each strain is also shown. The results were compared to comparative compounds A and B:

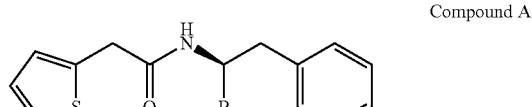

Compound A

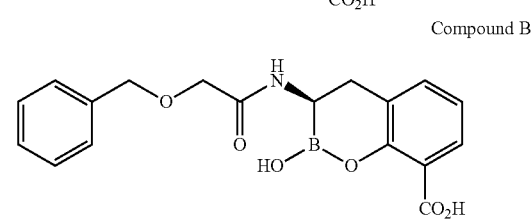

Compound B

TABLE 3

Activity of BLIs to potentiate biapenem against strains expressing class A (KPC) or class D (OXA-48) carbapenemases.

| | Biapenem MIC (μg/mL) | |
|---|---|---|
| | 32 | 16 |
| | BPM | BPM |
| | MPC$_1$ | MPC$_1$ |
| | KP1004 | OXA-48 |
| | KPC-2 | KP1086 |
| CPD A | X | Y |
| CPD B | X | Z |
| 2 | X | Y |
| 1 | X | Y |
| 3 | X | Y |
| 4 | X | Y |
| 8 | X | Y |
| 5 | X | Y |
| 6 | X | Y |
| 7 | X | Y |
| 9 | X | Z |
| 10 | X | Y |
| 11 | X | Y |
| 12 | X | Y |
| 13 | X | Y |
| 14 | X | Y |
| 15 | X | Y |
| 16 | X | Y |
| 17 | X | Y |
| 18 | Y | Y |
| 19 | X | Y |

X = MIC of less than 1 μg/mL
Y = MIC of 1 μg/mL to 10 μg/mL
Z = MIC of greater than 10 μg/mL

Example 20

Inhibitory Activity

K$_i$ values of inhibition of purified class A, C and D enzymes were determined spectrophotometrically using nitrocefin as reporter substrate. Purified enzymes were mixed with various concentrations of inhibitors in reaction buffer and incubated for 10 min at room temperature. Nitrocefin was added and substrate cleavage profiles were recorded at 490 nm every 10 sec for 10 min. The results of these experiments are presented in Table 5. These experiments confirmed that the described compounds are inhibitors with a broad-spectrum of activity towards various β-lactamases. The results were compared to comparative compounds A and B:

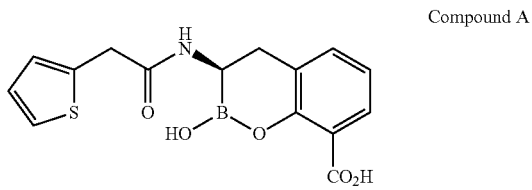 [SMILES: O=C(Cc1cccs1)N[C@H]1Cc2cccc(C(=O)O)c2OB1O]

Compound A

-continued

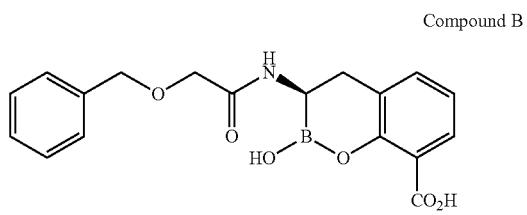

Compound B

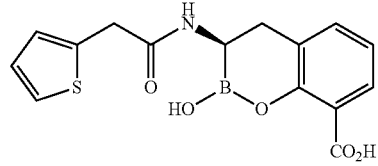

Compound A

Table 5 shows $MPC_{64}$ and EIs values for selected BLIs.

TABLE 4

Activity of BLIs (Ki, uM) to inhibit cleavage of nitrocefin by purified class A, C and D enzymes

| | Ki (CTX-M-14, NCF), uM | Ki (SHV-12, NCF), uM | Ki (TEM-10, NCF), uM | Ki (KPC-2, NCF), uM | Ki (P99, NCF), uM | Ki (CMY-2, NCF), uM | Ki (OXA-48, NCF), uM |
|---|---|---|---|---|---|---|---|
| CPD A | X | X | Y | Z | Y | X | X |
| CPD B | X | X | Y | Z | Y | Y | Y |
| 2 | Y | X | Y | Y | Y | Y | Y |
| 1 | Y | X | Y | Y | Y | Y | Y |
| 3 | Y | X | Y | Z | X | Y | X |
| 4 | Y | Y | Z | Z | Y | Y | Y |
| 8 | Y | X | Y | Z | Y | Y | X |
| 5 | Y | X | X | Z | X | X | X |
| 6 | Y | Y | Z | Z | Z | Z | Z |
| 7 | X | X | Y | Z | X | X | Y |
| 9 | Y | Y | Y | Z | Y | Y | Y |
| 10 | Y | X | Y | Z | Y | Y | Y |
| 11 | Y | X | Y | Z | X | X | X |
| 12 | X | X | Y | Y | X | Y | X |
| 13 | X | Y | Y | Z | Y | Y | X |
| 14 | X | X | Y | Z | Y | Y | Y |
| 15 | X | X | Y | Z | Y | Y | X |
| 16 | Y | X | Z | Z | Y | Y | Y |
| 17 | Y | Y | Z | Z | Y | Y | Y |
| 18 | Y | X | Y | Z | Y | Y | Y |
| 19 | Y | X | Y | Z | Y | ND | Y |

X = Less than 0.001 μM
Y = 0.001 μM to 0.01 μM
Z = Greater than 0.01 μM
ND = Not Determined

TABLE 5

MexAB-OprM Dependent Efflux of BLIs from *P. aeruginosa*

| | PAM1032/ KPC-2 Biapenem $MPC_{64}$ | PAM11154/ KPC-2 Biapenem $MPC_{64}$ | EI |
|---|---|---|---|
| CPD A | Z | X | Y |
| 3 | Z | X | Y |
| 2 | Z | Y | Y |
| 1 | Z | X | Y |
| 4 | X | X | X |
| 8 | Y | X | X |
| 5 | Y | X | X |
| 6 | X | X | X |
| 7 | Z | X | Y |
| 10 | Z | Y | X |
| 11 | Z | X | Y |
| 12 | Z | X | Y |
| 13 | Y | X | Y |
| 14 | Z | X | Z |
| 15 | Z | X | Y |
| 16 | X | X | X |
| 17 | Z | X | Y |
| 18 | Z | X | Y |

X = Less than 10
Y = 10 to 40
Z Greater than 40

Example 21

MexAB-OprM Dependent Efflux of BLIs

Efflux of BLIs from *Pseudomonas aeruginosa* by the MexAB-OprM efflux pump was also evaluated. The plasmid expressing the gene encoding KPC-2 was introduced into two strains of *P. aeruginosa*, PAM1032 and PAM1154 that overexpressed or lacked MexAB-OprM, respectively. Due to expression of KPC-2 both strains became resistant to biapenem. Biapenem is not affected by efflux in *P. aeruginosa* and both strains had the same biapenem MIC of 32 μg/ml. Potency of BLIs to potentiate biapenem in these strains was determined. Potency was defined as the ability of BLI to decrease MIC of biapenem 64-fold, from 32 μg/ml to 0.5 μg/ml, or $MPC_{64}$. The ratio of $MPC_{64}$ values for each BLI in PAM1032/KPC-2 (efflux proficient) and PAM1154/KPC-2 (efflux deficient) was determined to generate the Efflux Index (EI). The results were compared to comparative compound A:

Example 22

Inhibition of Serine Proteases

The effect of selected BLIs on the enzymatic activity of some common mammalian serine proteases was evaluated. Serine proteases used in the studies are shown in Table 6.

TABLE 6

List of Serine Proteases Used to Evaluate Selectivity of BLIs.

| Enzyme | Source | Catalog number |
|---|---|---|
| Trypsin | Calbiochem | 6502 |
| Chymotrypsin | Calbiochem | 230832 |
| Plasmin | MPBio | 19419890 |
| Thrombin | MPBio | 19491880 |
| Elastase | Calbiochem | 324682 |
| Urokinase | Calbiochem | 672112 |
| Tissue plasminogen activator (TPA) | Calbiochem | 612220 |
| Chymase | Enzo Lifescience | BML-SE281 |
| Dipeptidyl peptidase 7 (DPP7) | R&D Systems | 3438-SE |
| Dipeptidyl peptidase 8 (DPP8) | BPS Bioscience | 80080 |
| Dipeptidyl peptidase 9 (DPP9) | BPS Bioscience | 80090 |
| Neutrophil elastase | Calbiochem | 324681 |
| CathepsinA | R&D Systems | 1049-SE |
| CathepsinG | EMD Millipore | 219373 |

50 µl of the diluted enzyme was mixed with 50 µl of inhibitor at various concentrations and 50 µl of corresponding buffer (Table 7). Reaction mixtures were incubated for 10 min at 37° C. Subsequently, 50 µl of corresponding substrate (Table 7) was added and absorbance or fluorescence was monitored for 30 min on SpectraMax M2 plate reader (Molecular Devices). 4-(2-Aminoethyl)benzenesulfonyl fluoride hydrochloride (AEBSF) and leupeptin were used as positive controls. Rates of reaction were calculated and presented relative to "no treatment" control. IC50 values were calculated based on inhibitor concentration producing 50% of enzyme inhibition. IC50 values for selected BLIs are shown in Tables 8A and 8B. The results were compared to comparative compounds A and B:

Compound A

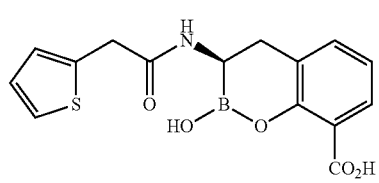

Compound B

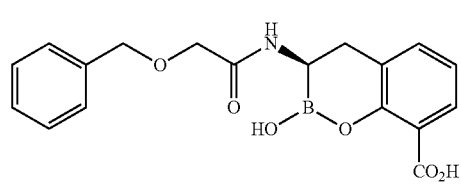

TABLE 8A

IC50 values (in µM) for serine proteases inhibition by selected BLIs

| Compound | IC50, uM | | | | | | |
|---|---|---|---|---|---|---|---|
| | Trypsin | Chymotrypsin | Thrombin | Plasmin | Elastase | Urokinase | Chymase |
| CPD A | Z | X | X | Z | ND | Z | X |
| CPD B | ND | Z | Z | ND | ND | ND | Y |
| 3 | Z | Z | Z | Z | Z | Z | Y |
| 4 | Z | Z | Z | Z | Z | Z | Z |
| 8 | Z | Z | Z | Z | Z | Z | Z |
| 5 | Z | Z | Z | Z | Z | Z | Y |
| 7 | Z | Z | Z | Z | Z | Z | Z |
| 11 | Z | Z | Z | Z | Z | Z | Z |
| AEBSF | 12.5 | 25 | 100 | >200 | 222 | 8.2 | 375 |
| Leupeptin | <0.27 | >200 | 15 | 5 | >200 | 22 | >200 |

X = IC50 of less than 300 µM
Y = IC50 of 300 µM to 800 µM
Z = IC50 of greater than 800 µM

TABLE 8B

IC50 values (in µM) for serine proteases inhibition by selected BLIs

| Compound | IC50, uM | | | | | | |
|---|---|---|---|---|---|---|---|
| | Neutrophil elastase | CathepsinA | Cathepsin G | HtrA2 | DPP7 | DPP8 | DPP9 |
| CPD A | Y | X | X | Z | Z | Y | Y |
| CPD B | Z | Y | Y | ND | ND | Y | Z |
| 3 | Y | X | X | Z | Z | Z | Z |
| 4 | Z | Z | Y | Z | Z | Z | Z |
| 8 | Z | Y | X | Z | Z | Z | Z |

TABLE 7

Enzyme substrates and buffers used in the study

| Enzyme | Buffer | Substrate | Substrate concentration, µM |
|---|---|---|---|
| Trypsin | 50 mM TrisHCl pH = 8.0, 10 mM CaCl2, 100 mM NaCl | N-Bz-R-AMC | 200 |
| Chymotrypsin | 20 mM TrisHCl pH = 8, 150 mM NaCl, 2.5 mM CaCl2 | Suc-AAPF-AMC | 10 |
| Plasmin | 100 mM TrisHCl pH = 7.5, 100 mM NaCl | H-D-VLK-pNA | 200 |
| Thrombin | 20 mM TrisHCl pH = 8, 150 mM NaCl, 2.5 mM CaCl2 | Benz-FVR-AMC | 10 |
| Elastase | 25 mM Tris-HCl pH pH 8.0 | Suc-AAPA-pNA | 50 |
| Urokinase | 50 mM Tris HCl, pH 8.5, 38 mM NaCl | NGK-pNA | 100 |
| Tissue plasminogen activator (TPA) | 30 mM Tris-HCl, pH 8.5, 30 mM imidazole, 130 mM NaCl | GK-pNA | 100 |
| Chymase | 100 mM Tris pH 8.0, 2M NaCl 0.01% Triton X-100 | Suc-AAPF-AMC | 40 |
| Dipeptidyl peptidase 7 (DPP7) | 50 mM Na—Ac pH 5.8 | H-Lys-Pro-AMC | 100 |
| Dipeptidyl peptidase 8 (DPP8) | 10 mM Tris pH 7.4, 10 mM MgCl2, 0.05% Tween-20 | Lys-Pro-AMC | 100 |
| Dipeptidyl peptidase 9 (DPP9) | 25 mM Tris pH 7.5, 0.1% BSA | Lys-Pro-AMC | 100 |
| Neutrophil elastase | 50 mM TrisHCl pH = 7.5; 1M NaCl | MeOSuc-AAVP-AMC | 30 |
| CathepsinA | 25 mM MES, 5 mM DTT, pH 5.5 | MCA-RPPGFSAFK-Dnp | 10 |
| CathepsinG | 50 mM Na—Ac, pH 5.8, 2 mM EDTA, 1 mM DTT | Suc-AAPF-AMC | 100 |

TABLE 8B-continued

IC50 values (in μM) for serine proteases inhibition by selected BLIs

| Compound | IC50, uM | | | | | | |
|---|---|---|---|---|---|---|---|
| | Neutrophil elastase | Cathepsin A | Cathepsin G | HtrA2 | DPP7 | DPP8 | DPP9 |
| 5 | Z | Y | X | Z | Z | Y | Z |
| 7 | Z | Y | Y | ND | Z | Y | Z |
| 11 | Z | Y | Y | ND | Z | Z | Z |
| 12 | ND | Y | X | ND | ND | ND | ND |
| 14 | ND | Y | Y | ND | ND | ND | ND |
| 15 | ND | Y | Y | ND | ND | ND | ND |
| AEBSF | Z | Y | Z | Z | Z | Z | Z |
| Leupeptin | Y | Y | ND | Z | Y | Y | Y |
| CathG inhibitor | ND | ND | X | ND | ND | ND | ND |

X = IC50 of less than 15 μM
Y = IC50 of 15 μM to 500 μM
Z = IC50 of greater than 500 μM Although the invention has been described with reference to embodiments and examples, it should be understood that numerous and various modifications can be made without departing from the spirit of the invention. Accordingly, the invention is limited only by the following claims.

What is claimed is:

1. A compound having the structure of formula I:

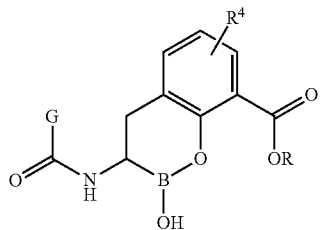

(I)

or pharmaceutically acceptable salt thereof, wherein:
G is selected from the group consisting of —H, —NR$^1$R$^2$, —CH$_2$N$_3$, —C(O)NR'R$^2$, —CH$_2$C(O)NR$^1$R$^2$, —CH$_2$S(O)$_2$NR$^1$R$^2$, —CH$_2$—Y—Z, —CH$_2$—Y—X, and —SR$^3$;
Y is selected from a group consisting of —S—, —S(O)—, —S(O)$_2$—, —O—, and —NR$^1$—;
R is selected from a group consisting of —H, —C$_{1-9}$alkyl, —CR$^1$R$^2$OC(O)C$_{1-9}$alkyl, —CR$^1$R$^2$OC(O)OC$_{1-9}$alkyl, and

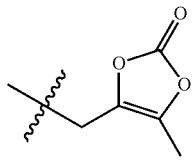 [SMILES: *Cc1oc(=O)oc1C]

R$^1$ and R$^2$ are each independently selected from the group consisting of —H and —C$_{1-4}$alkyl;
R$^3$ is —C$_{1-4}$alkyl;
R$^4$ is present 1 to 3 times and each R$^4$ is independently selected from the group consisting of —H, —C$_{1-4}$alkyl, —OH, —OC$_{1-4}$alkyl, and halogen;
Z is selected from the group consisting of aryl optionally substituted with C$_{1-4}$alkyl, amino, hydroxy, or halogen and heteroaryl optionally substituted with C$_{1-4}$alkyl, amino, hydroxy, or halogen;
X is selected from the group consisting of —C$_{1-4}$alkyl, —CH$_2$R$^5$, —CH(R$^5$)$_2$, and —C(R$^1$)$_3$; and
R$^5$ is selected from the group consisting of a halogen, cyano, and azido group.

2. The compound of claim 1, having the structure of (Ia):

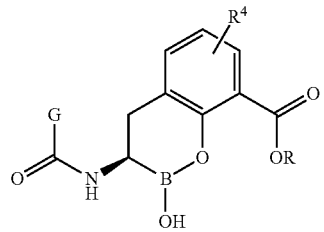

(Ia)

or pharmaceutically acceptable salt thereof.

3. The compound of claim 1, wherein R is H.
4. The compound of claim 1, wherein R$^4$ is H.
5. The compound of claim 1, wherein G is H.
6. The compound of claim 1, wherein G is —NH$_2$.
7. The compound of claim 1, wherein G is —C(O)NR$^1$R$^2$ and R$^1$ and R$^2$ are each independently selected from —H and C$_{1-4}$alkyl.
8. The compound of claim 7, wherein R$^1$ is —CH$_3$ and R$^2$ is —CH$_3$.
9. The compound of claim 1, wherein G is —CH$_2$C(O)NR$^1$R$^2$ and R$^1$ and R$^2$ are each independently selected from —H and C$_{1-4}$alkyl.
10. The compound of claim 9, wherein R$^1$ is —CH$_3$ and R$^2$ is —CH$_3$.
11. The compound of claim 1, wherein R$^3$ is CH$_3$.
12. The compound of claim 1, wherein:
G is Cl$_2$.Y—Z;
Y is —S—; and
Z is selected from the group consisting of imidazole, N-methylimidazole, aminoimidazole, triazole, N-methyl triazole, aminotriazole, tetrazole, N-methyltetrazole, aminotetrazole, thiazole, aminothiazole, thiadiazole, aminothiadiazole, oxazole, oxadiazole, pyridine, pyridazine, pyrimidine and pyrazine.
13. The compound of claim 12, wherein Z is N-methyltetrazole.
14. The compound of claim 12, wherein Z is thiadiazole.
15. The compound of claim 12, wherein Z is aminothiadiazole.
16. The compound of claim 1, wherein:
G is —CH$_2$.Y—X; and
Y is —S—.
17. The compound of claim 16, wherein X is CH$_3$.
18. The compound of claim 16, wherein X is CH$_2$CN.
19. The compound of claim 16, wherein X is CH$_2$N$_3$.
20. The compound of claim 16, wherein X is —CH$_2$F.
21. The compound of claim 16, wherein X is —CHF$_2$.
22. The compound of claim 16, wherein X is —CF$_3$.

23. The compound of claim 1, having the structure selected from the group consisting of:

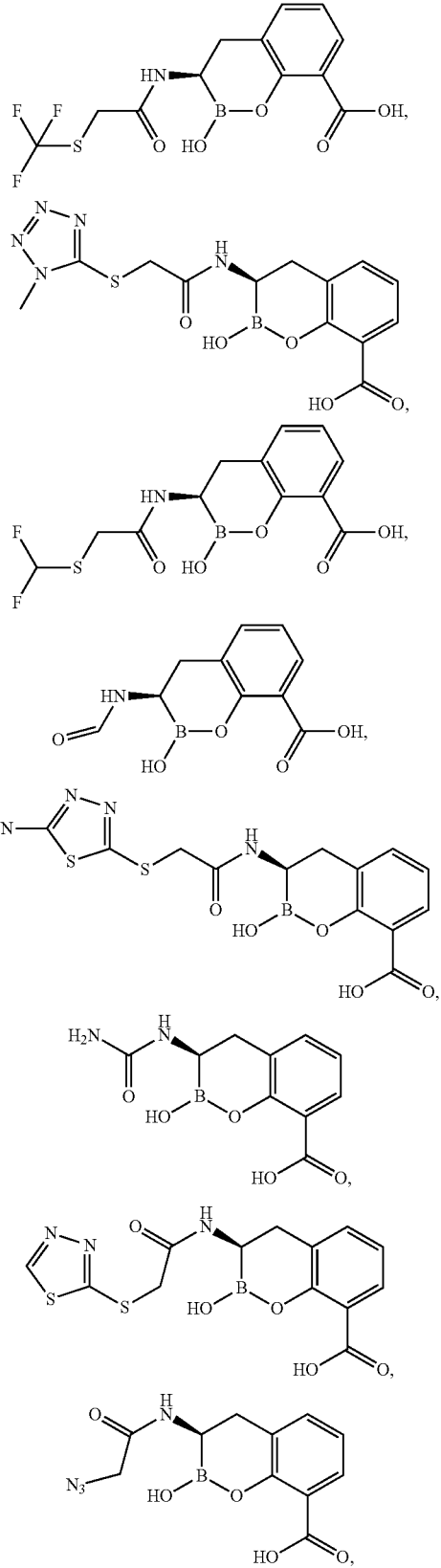

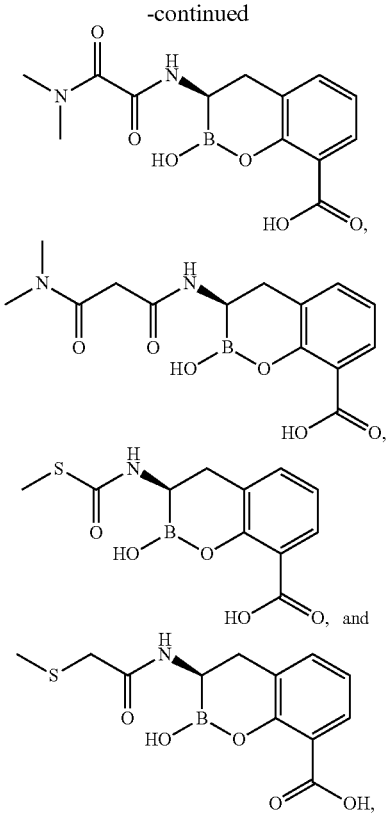

or pharmaceutically acceptable salts thereof.

24. The compound of claim 1, having the structure selected from the group consisting of

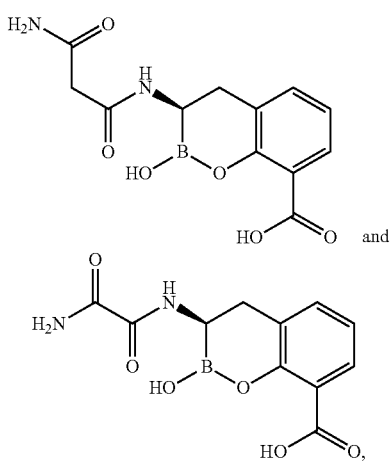

or pharmaceutically acceptable salts thereof.

25. A compound having the structure of formula II:

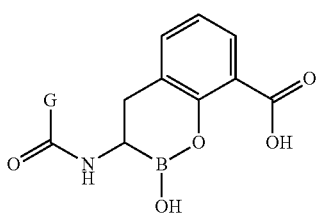

(II)

or pharmaceutically acceptable salt thereof, wherein:
G is selected from the group consisting of

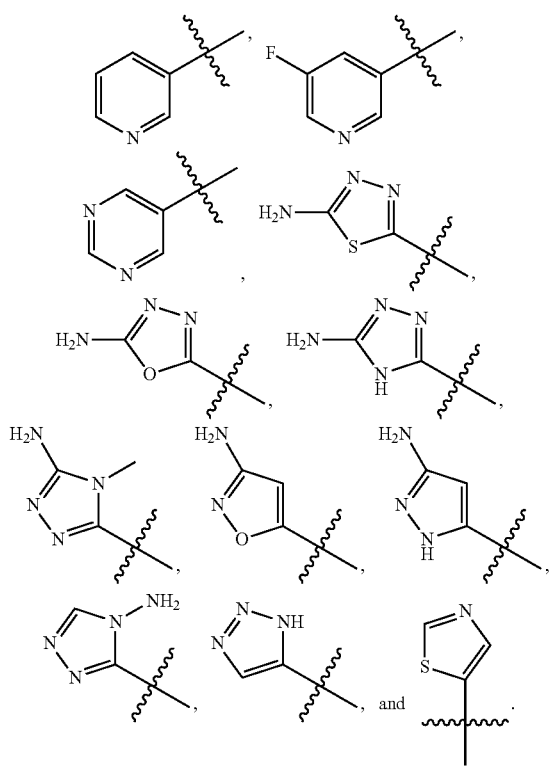

26. The compound of claim 25, having the structure of:

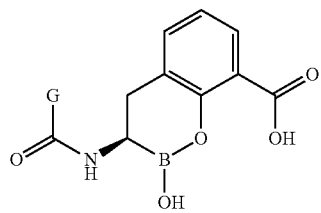

(IIa)

or pharmaceutically acceptable salt thereof.

27. The compound of claim 25, having the structure selected from the group consisting of:

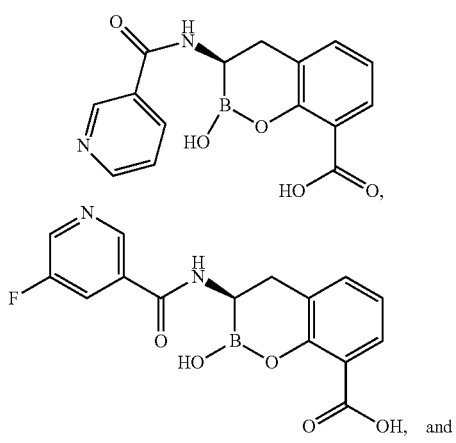

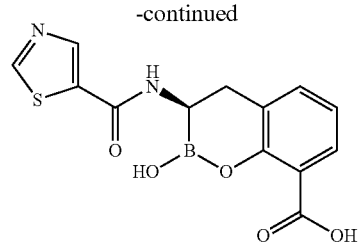

or pharmaceutically acceptable salt thereof.

28. The compound of claim 25, having the structure selected from the group consisting of:

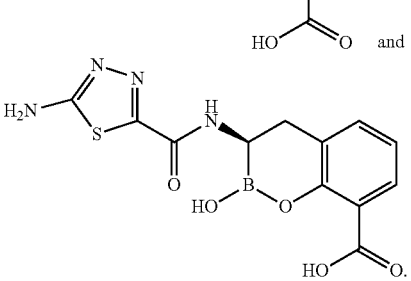

29. The compound of claim 25, wherein G is selected from the group consisting of

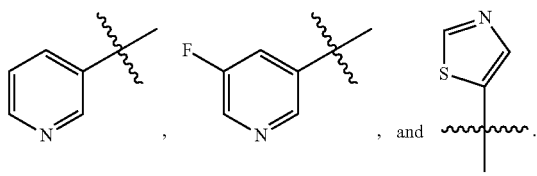 [SMILES: *c1cccnc1 ; *c1cncc(F)c1 ; *c1cncs1]

30. A pharmaceutical composition comprising a therapeutically effective amount of a compound of claim 1 and a pharmaceutically acceptable excipient.

31. The pharmaceutical composition of claim 30, further comprising an additional medicament.

32. The composition of claim 31, wherein the additional medicament is selected from an antibacterial agent, antifungal agent, an antiviral agent, an anti-inflammatory agent, or an anti-allergic agent.

33. The composition of claim 32, wherein the additional medicament is a β-lactam antibacterial agent.

34. The composition of claim 33, wherein the β-lactam is selected from Amoxicillin, Ampicillin, Pivampicillin, Hetacillin, Bacampicillin, Metampicillin, Talampicillin, Epicillin, Carbenicillin, Carindacillin, Ticarcillin, Temocillin, Azlocillin, Piperacillin, Mezlocillin, Mecillinam, Pivmecillinam, Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin, Dicloxacillin, Flucloxacillin, Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, Ceftiofur, Cefquinome, Cefovecin, RWJ-442831, RW1-333441, or RWJ-333442.

35. The composition of claim 33, wherein the β-lactam is selected from Ceftazidime, Biapenem, Doripenem, Ertapenem, Imipenem, Meropenem, or Panipenem.

36. The composition of claim 33, wherein the β-lactam is selected from Aztreonam, Tigemonam, BAL30072, SYN 2416, or Carumonam.

37. A method of treating a bacterial infection, comprising administering to a subject in need thereof, a compound according to claim 1 and a B-lactam antibacterial agent.

38. The method of claim 37, wherein the β-lactam is selected from Amoxicillin, Ampicillin, Pivampicillin, Hetacillin, Bacampicillin, Metampicillin, Talampicillin, Epicillin, Carbenicillin, Carindacillin, Ticarcillin, Temocillin, Azlocillin, Piperacillin, Mezlocillin, Mecillinam, Pivmecillinam, Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin, Dicloxacillin, Flucloxacillin, Oxacillin, Meticillin, Nafcillin, Faropenem, Tomopenem, Razupenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, Ceftiofur, Cefquinome, Cefovecin, RWJ-442831, RWJ-333441, or RWJ-333442.

39. The method of claim 37, wherein the β-lactam is selected from Ceftazidime, Biapenem, Doripenem, Ertapenem, Imipenem, Meropenem, or Panipenem.

40. The method of claim 37, wherein the β-lactam is selected from Aztreonam, Tigemonam, BAL30072, SYN 2416, or Carumonam.

41. The method of claim 37, wherein the subject is a mammal.

42. The method of claim 41, wherein the mammal is a human.

43. The method of claim 37, wherein the infection comprises a bacteria selected from *Pseudomonas acidovorans, Pseudomonas alcaligenes, Pseudomonas putida, Burkholderia cepacia, Aeromonas hydrophila, Francisella tularensis, Morganella morganii, Proteus mirabilis, Proteus vulgaris, Providencia alcalifaciens, Providencia rettgeri, Providencia stuartii, Acinetobacter baumannii, Bordetella pertussis, Bordetella parapertussis, Bordetella bronchiseptica, Haemophilus ducreyi, Pasteurella multocida, Pasteurella haemolytica, Branhamella catarrhalis, Borrelia burgdorferi, Kingella, Gardnerella vaginalis, Bacteroides distasonis, Bacteroides* 3452A homology group, *Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

44. The method of claim 37, wherein the infection comprises a bacteria selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus*.

\* \* \* \* \*